United States Patent
Yamagata et al.

(10) Patent No.: US 9,354,240 B2
(45) Date of Patent: May 31, 2016

(54) PROBE FOR ANALYZING BIOLOGICAL TISSUE AND METHOD FOR UTILIZING SAME

(75) Inventors: Youhei Yamagata, Miyagi (JP); Masafumi Goto, Miyagi (JP); Kimiko Watanabe, Miyagi (JP)

(73) Assignees: TOHOKU UNIVERSITY, Miyagi (JP); MEIJI SEIKA PHARMA CO., LTD., Tokyo (JP)

( * ) Notice: Subject to any disclaimer, the term of this patent is extended or adjusted under 35 U.S.C. 154(b) by 0 days.

(21) Appl. No.: 14/003,495

(22) PCT Filed: Mar. 15, 2012

(86) PCT No.: PCT/JP2012/001814
§ 371 (c)(1),
(2), (4) Date: Sep. 6, 2013

(87) PCT Pub. No.: WO2012/124338
PCT Pub. Date: Sep. 20, 2012

(65) Prior Publication Data
US 2013/0345087 A1 Dec. 26, 2013

(30) Foreign Application Priority Data
Mar. 16, 2011 (JP) ................. 2011-058080

(51) Int. Cl.
| | | |
|---|---|---|
| G01N 33/68 | (2006.01) | |
| C12N 9/52 | (2006.01) | |
| G01N 33/569 | (2006.01) | |
| C07K 14/435 | (2006.01) | |
| C12N 9/02 | (2006.01) | |
| C12N 9/50 | (2006.01) | |

(52) U.S. Cl.
CPC ...... *G01N 33/6887* (2013.01); *C07K 14/43595* (2013.01); *C12N 9/0069* (2013.01); *C12N 9/50* (2013.01); *C12N 9/52* (2013.01); *G01N 33/56966* (2013.01); *C07K 2319/60* (2013.01)

(58) Field of Classification Search
CPC .................. G01N 33/6887; G01N 33/56966; C12N 9/52; C12N 9/50; C07K 2319/60; C07K 9/0069; C07K 14/43595
USPC .......................................................... 506/9
See application file for complete search history.

(56) References Cited

U.S. PATENT DOCUMENTS

| | | |
|---|---|---|
| 5,753,485 A | 5/1998 | Dwulet |
| 6,458,547 B1 | 10/2002 | Bryan et al. |
| 2004/0053368 A1 | 3/2004 | Ishikawa et al. |
| 2005/0106636 A1 | 5/2005 | Stagljar et al. |
| 2006/0166214 A1 | 7/2006 | Kato et al. |
| 2007/0128596 A1 | 6/2007 | Roninson et al. |
| 2011/0294192 A1 | 12/2011 | Fukushima et al. |

FOREIGN PATENT DOCUMENTS

| | | |
|---|---|---|
| CN | 1761749 A | 4/2006 |
| CN | 1977167 A | 6/2007 |
| EP | 1348766 A1 | 10/2003 |
| JP | 09-508026 A | 8/1997 |
| JP | 2002-159297 A | 6/2002 |
| JP | 2005-521408 A | 7/2005 |
| JP | 2006-145545 A | 6/2006 |
| JP | 2009-077714 A | 4/2009 |
| WO | 96/00283 A1 | 1/1996 |
| WO | 98/24889 A1 | 6/1998 |
| WO | 02/14505 A1 | 2/2002 |
| WO | 2006006961 A1 | 1/2006 |
| WO | 2010/058707 A1 | 5/2010 |

OTHER PUBLICATIONS

The Molecular Probes Handbook, A Guide to Flourescent Probes and Labeling Technologies, 11th edition (2010), chapter 11 pp. 476-477, found at https://www.lifetechnologies.com/content/dam/LifeTech/global/technical-reference-library/Molecular%20Probes%20Handbook/chapter-pdfs/Ch-11-Cytoskeletal-Protein-Probes.pdf?icid=WE216841.*
Wolters et al. (Diabetologia, 1992, 35, pp. 735-742).*
Office action for Chinese Application No. 2012800136123 (PCT/JP2012001814), issued Dec. 3, 2014 (English translation included).
Krahn Katy Nash et al., Fluorescently labeled collagen binding proteins allow specific visualization of collagen in tissues and live cell culture, Anal Biochem, 2006, vol. 350 No. 2, pp. 177-185.
Goto et al., "Suito Bunri-yo Kosozai no Kassel Hyoka System no Kochiku" Sui-Suito Ishoku Kenkyukai Program—Shorokushum 2010, vol. 37, p. 53 together with English translation thereof.
Inoue et al., "Ultrastructure of Reichart's Membrane, a Multilayered Basement Membrane in the Parietal Wall of the Rat Yolk Sac", Journal of Cell Biology, vol. 97, 1983, pp. 1524-1537.
S.J. Hughes et al., "Comparison of the Collagen VI Content Within the Islet-Exocrine Interface of the Head, Body, and Tail Regions of the Human Pancreas", Transplant Proceedings, vol. 37, 2005, pp. 3444-3445.
S.J. Hughes et al., "Characterisation of Collagen VI within the Islet-Exocrine Interface of the Human Pancreas: Implication for Clinical Islet Isolation?", Transplantation, vol. 81(3), 2006, pp. 423-426.

(Continued)

*Primary Examiner* — Larry Riggs
*Assistant Examiner* — Karla Dines
(74) *Attorney, Agent, or Firm* — Pearne & Gordon LLP

(57) ABSTRACT

The present invention relates to a method for obtaining cells or cell populations having a high biological activity from a biological tissue by enzymatic isolation, and probes for use in the method; more specifically to a method for analyzing a biological tissue, comprising applying two or more probes respectively containing biological-component binding domains through which two or more proteins bind to a predetermined biological component, to an isolated biological tissue, and analyzing binding amounts of the probes to the biological tissue.

15 Claims, 14 Drawing Sheets

(56) References Cited

OTHER PUBLICATIONS

D. Brandhorst et al., "Adjustment of the Ratio Between Collagenase Class II and I Improves Islet Isolation Outcome" Transplantation Proceedings, vol. 37, 2005, pp. 3450-3451.
E. Linetsky et al., Improved Human Islet Isolation Using a New Enzyme blend, Liberase, Diabetes, vol. 46, 1997, pp. 1120-1123.
K. Watanabe, "Collagenolytic proteases form bacteria", Appl Microbiol Biotechnol, vol. 63, 2004, pp. 520-526.
N. Nishi et al., "Collagen-binding growth factors; Production and characterization of functional fusion proteins having a collagen-binding domain" Proc. Natl. Acad. Sci. USA; vol. 95, 1998, pp. 7018-7023.
Tuan et al., "Engineering, Expression and Renaturation of Targeted TGF-Beta Fusion Proteins" Connective Tissue Research, vol. 34, No. 1, 1996, pp. 1-9.
Han et al., "Refolding of a Recombinant Collagen-Targeted TGF-β2 Fusion Protein Expressed in *Escherichia coli*" Protein Expression and Purification vol. 11, 1997, pp. 169-178.
International Search Report for PCT/JP2012/001814 (English translation), published Sep. 20, 2012.
International Search Report issued in Japanese Patent Application No. PCT/JP2014/000527 dated Apr. 15, 2014.
Heide Brandhorst et al.,"The Importance of Tryptic-like Activity in Purified Enzyme Blends for Efficient Islet Isolation" Basic and Experimental Research, vol. 87, No. 3 dated 2009.
Partial supplementary European search report for European Application No. 12758377.1 (PCT/JP2012001814), mailed Jan. 30, 2015.
Meyer, T. et al., "Expression pattern of extracellular matrix proteins in the pancreas of various domestic pig breeds, the Goettingen Minipig and the Wild Boar," Annals of Transplantation, vol. 2, No. 3, 1997, pp. 17-26.
Van Suylichem, P.T.R. et al., "Amount and distribution of collagen in pancreatic tissue of different species in the perspective of islet isolation procedures", Cell Transplantation, vol. 4, No. 6, 1995, pp. 609-614.
Carter, J.D. et al., "A Practical Guide to Rodent Islet Isolation and Assessment," Biological Procedures Online, vol. 11, No. 1, 2009, pp. 3-31.
Yoshida, S. et al., "The Influence of Collagen III Expression on the Efficiency of Cell Isolation With the Use of Collagenase H", Transplantation Proceedings, vol. 46, No. 6, 2014, pp. 1942-1944.
Fujio, A. et al., "Collagenase H Is Crucial for Isolation of Rat Pancreatic Islets", Cell Transplantation, vol. 23, No. 10, 2014, pp. 1187-1198.
McCarthy, et al., "Tissue Dissociation Enzymes for Isolating Human Islets for Transplantation: Factors to Consider in Setting Enzyme Acceptance Criteria", Transplantation, vol. 91, No. 2, pp. 137-145, 2011.
Wolters, et al., "Different Roles of Class I and Class II Clostridium Histolyticum Collagenase in Rat Pancreatic Islet Isolation", Diabetes, vol. 44, No. 2, pp. 227-233, 1995.
Vos-Scheperkeuter, et al., "Histochemical Analysis of the Role of Class I and Class II Clostridium Histolyticum Collagenase in the Degradation of Rat Pancreatic Extracellular Matrix for Islet Isolation", Cell Transplantation, vol. 6, No. 4, pp. 403-412, 1997.
Extended European Search Report for Appl. No. EP 12758377 (PCT/JP2012001814), mailed Jun. 8, 2015 (12 pages).
Bauer, et al, Structural Comparison of ColH and ColG Collagen-Binding Domains from Clostridium histolyticum; Journal of Bacteriology, Jan. 2013, vol. 195, No. 2, pp. 318-327.
Knight, et al., The Collagen-binding A-domains of Integrins $\alpha1\beta1$ and $\alpha2\beta1$ Recognize the Same Specific Amino Acid Sequence, GFOGER, in Native (Triple-helical) Collagens; The Journal of Biological Chemistry, Jan. 7, 2000, vol. 275, No. 1, pp. 35-40.
Steffensen, et al., Human fibronectin and MMP-2 collagen binding domains compete for collagen binding sites and modify cellular activation of MMP-2; Matrix Biology, 2002, vol. 21, pp. 399-414.
Neil D. Rawlings, A large and accurate collection of peptidase cleavages in the MEROPS database; Database, 2009, vol. 2009, Article ID bap015, doi:10.1093/database/bap0015, pp. 1-14.

* cited by examiner

FIG.1

(A) ColGCBD (B) ColHCBD

A                 B

A (Negative control: PSB alone)

B (EGFP-Co1GCBD Light exposure time1/4.5s)

PROBE FOR ANALYZING BIOLOGICAL TISSUE AND METHOD FOR UTILIZING SAME

TECHNICAL FIELD

The present invention relates to a method for obtaining cells or cell populations having a high biological activity in high yield from a biological tissue by enzymatic isolation, and probes for the method.

BACKGROUND ART

Enzymatic isolation of cells and cell clusters from a biological tissue is useful for various purposes including transplantation of the cells and establishment of cell strains and in a wide variety of usages in the fields of therapy, diagnosis and examination. However, to dissociate a biological tissue and isolate cells or cell aggregates constituting the tissue, it is necessary to separate cells or cell aggregates to a desired level and isolate them from the cellular tissue. In separating cells and cell clusters from a biological tissue, the intercellular matrix is degraded by a mixture of proteases such as collagenase.

A biological tissue is constituted of cells and the intercellular matrix. The intercellular matrix, which is a substance for anchoring cells, includes structural materials and non-structural materials. The former ones include fibers such as a collagenic fiber, an elastic fiber and a reticular fiber; whereas the latter ones include so-called ground substances formed of sol- or gel-materials such as a glycoprotein and proteoglycan, for filling the space between fibers. A typical example of the intercellular matrix is a protein called collagen, which occupies about ⅓ of the weight of the total proteins in a living body. Collagen has a fiber structure, which is formally called a collagen fiber.

Tissues are roughly classified into four categories: an epithelial tissue, a supporting tissue, a muscular tissue and a nervous tissue. The epithelial tissue is a tissue covering the surface of a body, in which cells are densely arranged without the intercellular matrix interposed between them. The supporting tissue, which works for supporting organs, cells and the like, includes a connective tissue, a cartilage tissue, a bone tissue, blood and lymph. The muscular tissue is an integration of cells differentiated for purpose of contraction motion, in which the intercellular tissue occupies an extremely low ratio.

The muscular tissue is constituted of muscle cells, a connective tissue, blood vessels and nerve; however, it is primarily formed of muscle fibers. The nerve tissue is primarily constituted of the endoneurium and the perineurium, each containing a large amount of intercellular matrix (collagen). The connective tissue, which is a kind of supporting tissue, is constituted of adipose tissue and fibrous connective tissue (constituted of a collagen fiber and an elastic fiber) and roughly divided into hydrophobic connective tissue and dense connective tissue. The hydrophobic connective tissue is fibrous connective tissue having collagen fibers irregularly arranged therein and distributed in the subcutaneous tissue, mucosal tissue, nerve, outer membrane of blood vessel and interlobular tissue.

The content of collagen in the intercellular matrix varies depending upon the species, age, sex, tissue and living environment. However, it has not yet been sufficiently elucidated which type of collagen is included in which tissue and in which state of matrix in which amount. The feature of collagen resides in that amino acids constituting a peptide chain of a protein has a primary structure in which glycine repeatedly appears every third residue like "glycine-amino acid X-amino acid Y". It has been reported that there are about beyond 30 types of collagen proteins in a human body. The collagen most abundantly present in a body is fibrous type I collagen. Non-fibrous type IV collagen is also contained abundantly and mutually connected via an intermolecular disulfide bond, contributing to formation of a reticular tissue (Non Patent Literature 1). It is reported that Type IV collagen is present between pancreatic islets and the endocrine tissue (Non Patent Literatures 2 and 3).

It may be theoretically possible to determine the presence of a predetermined type of collagen in a target matrix by immuno-staining using antibodies against individual types of collagens. However, many types of collagens are present in wide variety types of multicellular animals. Thus, it is difficult to produce antibodies against collagens. This fact serves as an obstacle and renders it difficult to realize determination of collagen by immuno-staining.

Enzymes for degrading tissue, i.e., various types of crude collagenases derived from *Clostridium histolyticum* contain not only two types of collagenases but also various types of proteases (having collagen degradation activity and nonspecific protein degradation activity) and non-protease components (e.g., phospholipase). By virtue of the crude collagenase, cells and cell populations are enzymatically separated from a biological tissue.

In enzymatically separating individual cells or cell populations form a biological tissue, two types of collagenases (ColG and ColH) are reported to have important roles in attaining the yield and keeping biological activity of the cells and cell populations to be separated, and thus the quantitative ratio of them has a significant effect upon the yield and activity (Non Patent Literature 4). Also, in separating pancreatic islets from the pancreatic tissue, two types of collagenases produced by *Clostridium histolyticum* are used (Non Patent Literature 5, Patent Literatures 1 and 2). The present inventors have so far found that pancreatic islets with high quality can be separated by optimizing the quantitative ratio of the two types of collagenases.

It has been reported that different collagenases have mutually different collagen binding domains (Non Patent Literature 6). Up to the present, various fusion proteins formed of a functional protein and a collagen binding domain have been prepared for targeting and delivery system (DDS). Examples thereof include a collagen bindable cell growth factor (Non Patent Literature 7) prepared by binding bFGF or EGF to a collagen binding domain of a collagenase derived from *Clostridium histolyticum*; a fusion protein formed of bovine von Willebrand factor-derived collagen binding deca-peptide and TGF-β (Non Patent Literatures 8 and 9); and a sustained-release cell growth factor supply agent (Patent Literature 3) prepared by binding a functional peptide to a collagen binding domain of fibronectin. As described above, fusion proteins with a collagen binding domain have been prepared for targeting and visualization of tissues; however, they have never been used for analysis and separation of a biological tissue.

In order to isolate a specific tissue and cells without damaging them, it is necessary to degrade the intercellular matrix present around the tissue and cells. However, it is not easy to degrade the intercellular matrix alone without degrading and damaging the surface of the desired cells. Particularly, in the case of a human organ, the proteolytic degradability varies depending upon e.g., the age, sex, habit and medical history. Thus, isolation has to be performed empirically by determining the type of enzyme and reaction time thereof.

To diabetic patients, a therapy (pancreatic islet transplantation) for transplanting pancreatic islets isolated from the pancreas is applied. For transplantation of pancreatic islets, it is essential to separate cell clumps called pancreatic islets present in the pancreatic tissue. The pancreatic tissue must be degraded without giving any damage to pancreatic islets to separate them. However, the state of the intercellular matrix significantly varies depending upon the type of animal, site of the tissue, age or sex of an individual body and growth environment. Particularly, collagen significantly changes in physical properties depending upon aging. Nevertheless, to pancreatic tissues different in state, a predetermined quantitative ratio of enzymes is applied in accordance with a protocol (except that degradation time alone is changed) and an enzymatic treatment is performed while visually checking the degree of degradation of the pancreas. For this reason, the quantity and quality of the pancreatic islets thus obtained vary depending upon the medical institution, medical workers and the state of the target pancreas.

If the type and quantity of protease to be used can be accurately and easily found from the protein composition of the extracellular matrix or organ to be degraded, target cells and the like can be isolated while maintaining high activity.

CITATION LIST

Patent Literature

Patent Literature 1: WO96/00283
Patent Literature 2: WO98/24889
Patent Literature 3: WO02/014505

Non Patent Literature

Non Patent Literature 1: Inoue et al., J Cell Biol, 97, 1524-1537 (1983)
Non Patent Literature 2: S J Hughes, P McShane, Transplant Proceedings, 37, 3444-34445 (2005)
Non Patent Literature 3: S J Hughes, A Clark, P McShane, Transplantation, 81(3) 423-426 (2006)
Non Patent Literature 4: D Brandhorst et al., Transplantation Proceedings, 37(8), 3450-3451 (2005)
Non Patent Literature 5: E Linetsky et al., Diabetes, 46, 1120-1123 (1997)
Non Patent Literature 6: K Watanabe, Appl Microbiol Biotechnol, 63, 520-526 (2004)
Non Patent Literature 7: N Nishi, O Matsushita, K Yuube, H Miyanaka, A Okabe, F Wada, Proc Natl Acad Sci USA; 95(12):7018-7023 (1998)
Non Patent Literature 8: Tuan et al., Connective Tissue Research, 34(1), 1-9 (1996)
Non Patent Literature 9: Han et al., Protein Expression and Purification 11, 169-178 (1997)

SUMMARY OF INVENTION

Technical Problem

An object of the present invention is to provide a means for quickly and efficiently separating cells and cell populations having a high biological activity from a biological tissue; more specifically, to obtain target cells and cell populations in high yield without decreasing the physiological activity of physiologically active substances in a biological tissue, cells or/and organs.

Solution to Problem

The inventors prepared probes for analyzing biological components using fusion proteins of substrate binding domains (biological-component binding domains) that two types of enzymes have, and visualization proteins. The inventors then found that target cells and cell populations can be more efficiently separated while maintaining a high biological activity by analyzing the binding amounts of probes and predicting action of the enzyme to a biological tissue, thereby determining, e.g., an optimal quantitative ratio of enzymes and action time.

In short, the present invention relates to a method for analyzing a biological tissue, which includes applying two or more probes respectively containing biological-component binding domains through which two or more proteins bind to a specific biological component, to an isolated biological tissue and analyzing binding amounts of the probes to the biological tissue.

The probes to be used in the present invention are designed to be visualized by a molecule imaging technique known in the art. More specifically, the probes are labeled with visualization molecules such as a fluorescent molecule, a luminescent molecule, a positron nuclide and a radioisotope.

Examples of the visualization molecules include fluorescent molecules such as GFP, EGFP, YFP, BFP, CFP, DsRED, tdTomato and RFP, and luminescent molecules such as a luciferase protein, but are not limited to these. The luciferase protein preferably has a peak wavelength and luminescent intensity different from those of a wild type luciferase present in nature.

A fluorescent molecule and a luminescent molecule may be used alone. Alternatively, a fluorescent molecule (energy receiving protein) may be used in combination with a self-luminescent molecule (energy generating protein) such as luciferase. In this case, both molecules are preferably linked to each other with an appropriate linker interposed between them.

As the biological-component binding domain to be used in a probe, a binding domain of a protease or a collagen binding domain of an in-vivo protein such as fibronectin may be mentioned. The specific examples of the former one include a collagen binding domain that *Clostridium*-derived collagenase has, such as collagen binding domains of *Clostridium histolyticum*-derived collagenase G and collagenase H.

Note that the collagen binding domain to be used in a probe may be a part of the domain (partial sequence) as long as the object and effect of the present invention can be attained. Such a part of the collagen binding domain is included in the term of "collagen binding domain".

The amino acid sequences of collagen binding domains of *Clostridium histolyticum*-derived collagenase G and collagenase H, which are specific examples of the substrate binding domain to be used in the present invention, are described in SEQ ID NO: 1 and SEQ ID NO: 2.

When a visualization molecule is a protein, a biological-component binding domain can be fused with the visualization molecule (protein) and used as a fusion protein.

In a probe, the sequence of a biological-component binding domain is repeated 1 to 100 times, and preferably 1 to 20 times.

In the analysis method of the present invention, two or more probes may be separately or simultaneously applied to a biological tissue. Furthermore, the binding amounts of individual probes may be separately or simultaneously measured. Preferably, two or more probes are labeled with different visualization molecules and simultaneously applied, and the binding amounts of them are simultaneously measured.

The present invention also provides a method for separating cells or cell populations from a biological tissue by the analysis method of the present invention. The separation method of the present invention is characterized by analyzing a biological tissue by the above analysis method, determining the quantitative ratio of enzymes (enzymes from which the substrate binding domains contained in the probes are derived) based on the analysis results, and applying the enzymes in the quantitative ratio to the biological tissue, thereby separating target cells or cell populations.

The present invention further provides a probe set for analyzing a biological tissue, constituted of the aforementioned two or more probes, and a biological tissues separation kit containing, e.g., the probe set and enzymes.

Advantageous Effects of Invention

Each of the probes to be used in the present invention contains a biological-component binding domain. It specifically binds to binding sites of a predetermined enzyme in a biological tissue and emits fluorescence or luminescence. Based on observation of fluorescence or luminescence emitted from each of the probes corresponding to the predetermined enzyme, affinity of the enzyme for a biological tissue and actions of enzyme can be analyzed. To describe more specifically, probes are incubated together with a small amount of frozen pieces of a target tissue to stain them. The binding states of the probes are analyzed based on the color tone and fluorescent intensity on the tissue pieces. Based on the analysis, the quantitative ratio and action time of the enzymes suitable for degradation can be computationally obtained.

More specifically, according to the present invention, the type and amount of protease to be used can be accurately and easily found based on the binding properties of probes to the extracellular matrix or of the protein of a tissue to be separated. In this manner, target cells and cell populations can be quickly and easily isolated from a biological tissue while maintaining a high activity. For example, in the case of transplanting pancreatic islets, an enzymatic treatment can be made in accordance with the state of a target pancreatic tissue, and indexing of the state of a pancreatic tissue for attaining separation of high-quality pancreatic islets constantly in a large amount can be established.

BRIEF DESCRIPTION OF DRAWINGS

FIG. 1 shows constitutions of (A) ColGCBD (nucleotide sequence (SEQ ID NO: 21) and amino acid sequence (SEQ ID NO: 1)) and (B) ColHCBD (nucleotide sequence (SEQ ID NO: 22) and amino acid sequence (SEQ ID NO: 2)).

Figure 2:
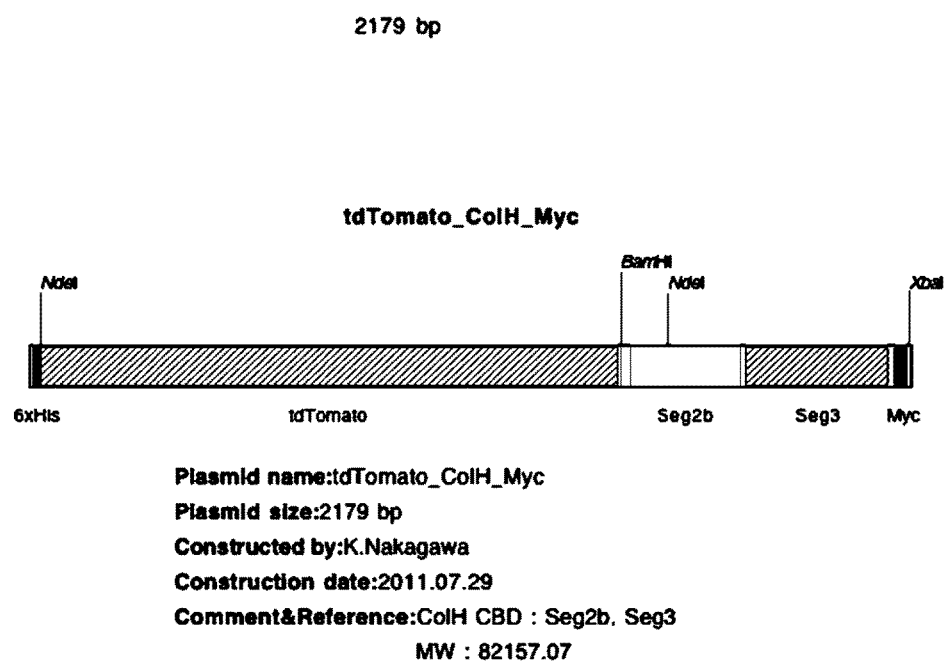
FIG. 2 shows a schematic view of the sequence of tdTomatoColH CBD.

The specification incorporates the content described in the specification of Japanese Patent Application No. 2011-058080 based on which the priority right of the present application is claimed.

DESCRIPTION OF EMBODIMENTS

1. Analysis Method for Biological Tissue

In the present invention, two or more probes respectively containing biological-component binding domains through which two or more proteins bind to a predetermined biological component are used to analyze the binding amounts (affinity) of a biological tissue to the probes. The results are applied to degradation of the biological tissue and isolation of cells and cell populations.

Herein, the "two or more proteins binding to a predetermined specific biological component" refers to intercellular matrix proteins such as fibronectin and integrin, and enzymes such as a protease. These proteins each have a site (domain) specifically binding to the corresponding ligand and substrate. The site will be described as "a biological-component binding domain" in the specification.

In isolating cells and cell populations from a biological tissue, in most cases, a plurality of enzymes are usually used. However, the action of each enzyme (sensitivity of a tissue) significantly varies depending upon the site and state of the biological tissue to which the enzyme is to be applied. Thus, to quickly and efficiently separate target cells and cell populations while maintaining a high biological activity, an optimal consumption, use ratio, action time of the enzyme and others are desirably determined in advance. The probes of the present invention allow for easily determination of such an optimal consumption, use ratio and action time of the enzyme.

The target "biological tissue" to be used in the present invention is not particularly limited, and includes a wide variety of tissues of multicellular animals (e.g., mammals, birds, reptiles and fish) such as liver, pancreas, kidney, tooth lap tissue, liver, pancreas, skin, cartilage, bone and nervous tissue. Furthermore, not only tissues isolated from a living body but also tissues artificially constructed, such as ES cell tissue and a tissue of fibroblast cells serving as a material for iPS cells are also included.

The present invention employs "two or more probes" respectively containing biological-component binding domains (for example, different enzyme-substrate binding sites) through which two or more proteins bind to a predetermined biological component. The biological-component binding domains to be used in the probes are appropriately selected depending upon the purpose of analysis.

For example, in analyzing a biological tissue prior to enzymatic digestion (degradation) of the biological tissue and separation of cells and cell populations, probes comprising a substrate binding domain of the protease to be used for such enzymatic digestion and separation of cells is used.

Examples of protease to be used in degradation of a tissue include collagenase, trypsin, chymotrypsin, dispase, elastase, papain, pronase, thermolysin, subtilisin, bromelain, phytin and thermitase. Examples of collagenase particularly include *Clostridium histolyticum*-derived collagenase G and collagenase H, *actinomyces*-derived collagenase and *Clostridium perfringens*-derived collagenase. Most of the primary structures of substrate binding sites of these enzymes have already been analyzed. Using the structural information, those skilled in the art can design a probe.

The probe bound to a biological tissue is visualized by a molecular imaging technique known in the art. Owing to visualization, the binding amount of probe can be easily determined without damaging the tissue. The probe is labeled by an appropriate visualization molecule such as a fluorescent molecule, a luminescent molecule and a radioisotope such as a positron nuclide. How to design a probe will be more specifically described in the following section.

Two or more probes may be separately or simultaneously applied to a biological tissue. Furthermore, the binding amounts of probes may be separately or simultaneously measured. However, in view of quick and simple measurement, it is preferable that two or more probes be labeled with different visualization molecules and simultaneously applied to a biological tissue, and that the binding amounts of them be simultaneously measured.

In the present invention, the aforementioned two or more probes are applied to a biological tissue isolated, and the binding amounts (affinity) of the probes to the biological tissue are analyzed. The results are applied to degradation of a biological tissue and isolation of cells and cell populations. To describe more specifically, the binding amount ratio of two or more probes to a biological tissue is obtained by the analysis. Based on the binding amount ratio, the optimal quantitative ratio of enzymes to be used for degradation of the biological tissue and isolation of cells and cell populations is determined. The binding ratio of the probes has a correlation with the quantitative ratio of enzymes. The higher the binding ratio is, the higher the optimal quantitative ratio of enzymes is. However, since enzymes mutually differ in number of units, titer (efficacy unit/mg), optimal temperature, optimal pH and action time, the quantitative ratio of the enzymes to be used is finally determined under comprehensive consideration of these factors and the binding ratio of probes. If the binding ratio of probes can be obtained by the present invention, such an optimal quantitative ratio can be determined by those skilled in the art.

2. Probe Set for Analysis of Biological Tissue

The probe set of the present invention is constituted of two or more probes. Each of the probes contains a different biological-component binding domain (one of the biological-component binding domains of two or more proteins binding to a predetermined biological component) and a visualization molecule selected from a fluorescent molecule, a luminescent molecule and a radioisotope including a positron nuclide.

The substrate binding domain of an enzyme is appropriately selected in accordance with the purpose of analysis. In analyzing a biological tissue prior to enzymatic digestion (degradation) of a biological tissue and separation of cells and cell populations, probes comprising a substrate binding domain of a protease used in such enzymatic digestion and separation of cells is used.

Examples of such a protease include collagenase, trypsin, chymotrypsin, dispase, elastase, papain, pronase, thermolysin, subtilisin, bromelain, phytin and thermitase. Examples of collagenase particularly include *Clostridium histolyticum*-derived collagenase G and collagenase H, and *actinomyces*-derived collagenase and *Clostridium perfringens*-derived collagenase. Most of the primary structures of substrate binding sites of these enzymes have already been analyzed. Using the structural information, those skilled in the art can design probes. As examples, the amino acid sequences of *Clostridium histolyticum*-derived collagenase G and collagenase H are described in SEQ ID NO: 1 and SEQ ID NO: 2, respectively.

It is preferable that a probe contains 1 to 100 repeats, particularly 1 to 20 repeats of a substrate binding domain (for example, collagen binding domain) or a part thereof.

As the visualization molecule, a fluorescent molecule, a luminescent molecule and a positron nuclide to be used in molecule imaging technique can be used.

As the fluorescent molecule, a fluorescent protein such as GFP, EGFP, YFP, BFP, CFP, DsRED, tdTomato and RFP or a fluorescent marker such as Alexa350, dimethylamino coumarin, 5/6-carboxy-fluorescein, Alexa488, ATT0488, DY-505, 5/6-carboxyfluorescein, Alexa488, Alexa532, Alexa546, Alexa555, ATT0488, ATT0532, tetramethylrhodamine, Cy3, DY-505, DY-547, Alexa635, Alexa647, ATTO600, ATT0655, DY-632, Cy5, DY-647, Cy5.5 can be used for visualization.

As the luminescent molecule, a luminescent enzyme such as luciferase can be used. As luciferase, luciferase derived from various luminescent organisms such as *Cypridina*, Hoplophoridae, luminescent insects (e.g., lightning bug, Pityobiinae), luminescent earthworm, *Latia*, pus shiitake, *Aequorea victoria* (Aequorin) can be mentioned. A modified luciferase having a peak wavelength and luminescent intensity different from a wild-type luciferase is preferably used.

A fluorescent protein such as GFP requires an external light source for emitting fluorescence; however, luciferase oxidizes luciferin to emit light by itself. A technique of emitting light from GFP without an external light source by binding luciferase to GFP is also developed, and thus such a technique may be applied (WO2004/22600, WO2004/052934).

Other than these, many techniques are known with respect to visualization of a protein (WO01/46694, National Publication of International Patent Application No. 2006-518209, National Publication of International Patent Application No. 2005-525111, Japanese Patent Laid-Open No. 2008-283959). These known techniques can be used.

As the radioisotope, a positron nuclide employed in imaging using PET can be used. Examples of the positron nuclide include $^{15}O$, $^{13}N$, $^{13}C$, $^{18}F$, $^{62}Cu$, $^{68}Ga$ and $^{82}Rb$. A conventional tag known in the art and frequently used in a PET probe can be used.

If a protein molecule is used as a visualization molecule, a biological-component binding domain (collagen binding domain) may be fused with the visualization molecule to constitute a fusion protein. A method for producing a fusion protein is known in the art (as described above, N Nishi, et al., Proc Natl Acad Sci USA; 95(12):7018-7023 (1998), Tuan et al., Connective Tissue Research, 34(1), 1-9 (1996), Han et al., Protein Expression and Purification 11, 169-178). Thus, those skilled in the art can easily produce a fusion protein in accordance with these conventional techniques.

3. Method for Separating Cells or Cell Populations from Biological Tissue

The present invention also provides a method for efficiently separating desired cells or cell populations from a biological tissue, by analyzing the biological tissue by use of the aforementioned analysis method and determining the quantitative ratio and action time of enzymes to be used, based on the analysis results.

Since the affinity of the tissue for an enzyme is suggested by the binding amount of probe, the quantitative ratio and action time of enzymes in accordance with the purpose can be predicted based on the affinity for each of the enzymes.

4. Biological Tissue Separation Kit

The present invention also provides a kit to be used in the aforementioned method for separating cells or cell populations from a biological tissue.

The kit of the present invention consists of one or two or more elements selected from reagents and tools used in the method for separating a biological tissue of the present invention, such as the probe set of the present invention, an enzyme used in separating a biological tissue and having a substrate binding domain used as a constitution element of a probe, and a buffer, as constitutional elements.

EXAMPLES

Now, the present invention will be more specifically described by way of Examples below; however, the present invention is not limited to these Examples.

Example 1

Preparation of Probe by Use of EGFP

[Preparation EGFP-ColGCBD Probe]
(1) Method for Constructing EGFP-ColGCBD

First, preparation of a probe (EGFP-ColGCBD) for *Clostridium histolyticum*-derived collagenase G labeled with EGFP will be described.

First, based on the FLAG sequence, two oligo DNAs: 5'-TCGACGATTATAAAGATGATGATGATAAAT-3' (SEQ ID NO: 3) and 5'-CTAGATTTATCATCATCATCTT-TATAATCG-3' (SEQ ID NO: 4) were synthesized. Each of the oligo DNAs was dissolved in TE so as to obtain a concentration of 100 μM. Then, 10 μl of oligo DNA, 3 μl of 10×T4 polynucleotide kinase buffer (manufactured by Nippon Gene), 0.3 μl of 0.1 M ATP, 2 μl of T4 polynucleotide kinase (20 U, Nippon Gene) and 14.7 μl of $H_2O$ were mixed and kept at 37° C. for one hour. An aliquot (10 μl) was taken from each of the reaction solutions and the aliquots were mixed. The solution mixture was maintained at 100° C. for 5 minutes and directly cooled gradually to room temperature. This was designated as insert solution 1.

To 10 μl of pCold2 (TAKARA Bio), 10 μl of 10× Tango buffer (manufactured by Fermentas), 1 μl of SalI (Fermentas), 1 μl of XbaI (Fermentas) and 28 μl of $H_2O$ were added, and a reaction was carried out at 37° C. for 5 hours. After completion of the reaction, to the reaction solution, 150 μl of TE was added; further 250 μl of a phenolic/chloroform/isoamyl alcohol (25:24:1) solution was added and sufficiently stirred. Thereafter, the mixture was centrifuged at room temperature for 5 minutes and at 16,000 g, and the supernatant was collected. To the supernatant collected, 20 μl of a 3M sodium acetate solution was added, and 450 μl of cold ethanol was added. The mixture was allowed to stand still on ice for 5 minutes, and then centrifuged at 16,000 g and at 4° C. for 5 minutes to collect a precipitation.

The precipitation was washed with 70% cold ethanol, and then dissolved in 40 μl of $H_2O$. To this, 5 μl of 10×BAP buffer (manufactured by TOYOBO CO. LTD.) and 5 μl of bacterial alkaline phosphatase (TOYOBO) were added. Reaction was carried out at 65° C. for one hour. The whole amount of reaction solution was subjected to 0.8% agarose electrophoresis. After completion of the electrophoresis, staining with an ethidium bromide solution was performed. After the position of a band was checked, the agarose gel was cut out. Recovery from the agarose gel was performed by use of the gel/PCR purification kit manufactured by Viogene. Elution was performed with 40 μl of EB in accordance with the accompanying protocol.

The eluate thus obtained was designated as vector solution 1. Vector solution 1 (9 μl), 1 μl of insert solution 1 and 10 μl of Ligation convenience solution (Nippon gene) were mixed and kept at 16° C. for 30 minutes. *Escherichia coli* DH5α was transformed with this solution. The *Escherichia coli* thus transformed was inoculated in 2 ml of LB medium sterilized by an autoclave and containing ampicillin, which was sterilized by a sterilized filter of 0.22 μm so as to obtain a final concentration of 100 μg/ml, cultured at 37° C. overnight, and then centrifuged at 10,000 g for one minute to collect bacterial cells. From the bacterial cells thus collected, plasmids were recovered by use of the mini plus plasmid DNA extraction kit manufactured by Viogene. Elution was performed with 100 μl of EB. To 10 μl of an aliquot taken from the eluate, 2 μl of 10× Tango buffer, 1 μl of XbaI and 7 μl of $H_2O$ were added and maintained at 37° C. for 3 hours. The reaction solution was subjected to 0.8% agarose gel electrophoresis, and a single band emerged in the vicinity of 4 kbp was cut out. Recovery was performed by use of the gel/PCR purification kit manufactured by Viogene. Elution was performed with 50 μl of EB. To 10 μl of the eluate, 10 μl of Ligation convenience solution was added and maintained at 16° C. for 30 minutes.

Using the solution, *Escherichia coli* DH5α was transformed again. The *Escherichia coli* thus transformed was inoculated in 2 ml of LB medium sterilized by an autoclave and containing ampicillin, which was sterilized by a sterilized filter of 0.22 μm so as to obtain a final concentration of 100 μg/ml, cultured at 37° C. overnight, and then centrifuged at 10,000 g for one minute to collect bacterial cells. From the bacterial cells thus collected, plasmids were recovered by use of the mini plus plasmid DNA extraction kit manufactured by Viogene. Elution was performed with 100 μl of EB. To 10 μl of an aliquot taken from the eluate, 3 μl of 10×K buffer (TAKARA Bio), 1 μl of BamHI (TAKARA Bio), 1 μl of EcoRI (TAKARA Bio) and 15 μl of $H_2O$ were added and reacted at 37° C. overnight. After completion of the reaction, extraction was performed with the equal amount of phenol/chloroform/isoamyl alcohol. To the obtained upper layer, 3 μl of 3M sodium acetate was added, and 70 μl of cold ethanol was added. The mixture was allowed to stand still on ice for 5 minutes, and then centrifuged at 16,000 g and at 4° C. for 5 minutes to collect a precipitation. The precipitation was washed with 70% cold ethanol, and then dissolved in 40 μl of $H_2O$. To this, 5 μl of 10×BAP buffer (TOYOBO) and 5 μl of bacterial alkaline phosphatase (TOYOBO) were added. A reaction was performed at 65° C. for one hour. The whole amount of reaction solution was subjected to 0.8% agarose electrophoresis with TAE buffer, and staining with an ethidium bromide solution was performed. After the position of a band was checked, the agarose gel was cut out. Recovery from the agarose gel was performed by use of the gel/PCR purification kit manufactured by Viogene. Elution was performed with 30 µl of EB in accordance with the accompanying protocol. The resultant eluate was designated as vector solution 2.

In the meantime, 0.5 µl of 100 µM 5'-AAAGAACGGATC-CACAACAACACCTATAACTAAAG-3' (primer 1: SEQ ID NO: 5), and 0.5 µl of 100 µM 5'-AAGCAGAGATGAAT-TCTTTATTTACCCTTAACTCATAG-3' (primer 2: SEQ ID NO: 6), 1 µl of a plasmid that had already been cloned and contained the whole length of a gene encoding *Clostridium histolyticum* collagenase G, 8 µl of dNTP mix (TAKARA Bio), 1.0 µl of PrimeStar HS (TAKARA Bio), 20 µl of 5M betain and 49 µl of H$_2$O were mixed, and the reaction consisting of 98° C., 2 min (the first step), 98° C., 10 sec (the second step), 55° C., 5 sec (the third step) and 72° C. and 90 sec (the fourth step) was performed, and a process from the second step to the fourth step was continuously repeated 35 times.

The resultant PCR fragments were purified by use of the gel/PCR purification kit manufactured by Viogene. Elution was performed with 50 µl of EB. To the aliquot (10 µl) of the resultant eluate, 3 µl of 10×K buffer (TAKARA Bio), 1 µl of BamHI (TAKARA Bio), 1 µl of EcoRI (TAKARA Bio) and 15 µl of H$_2$O were added, and a reaction was performed at 37° C. overnight. The whole amount of reaction solution was subjected to 0.8% agarose electrophoresis with TAE buffer, and stained with an ethidium bromide solution. After the position of a band was checked, the agarose gel was cut out. Recovery from the agarose gel was performed by use of the gel/PCR purification kit manufactured by Viogene. Elution was performed with 30 µl of EB in accordance with the accompanying protocol. The eluate was designated as insert solution 2.

To 5 µl of vector solution 2 and 5 µl of insert solution 2, 10 µl of Ligation convenience solution was added. The reaction was performed at 16° C. for 30 minutes. After completion of the reaction, using the ligation solution, *Escherichia coli* DH5α was transformed. The resultant transformed strain was inoculated in 2 ml of LB medium sterilized by an autoclave and containing ampicillin, which was sterilized by a sterilized filter of 0.22 µm so as to obtain a final concentration of 100 µg/ml, cultured at 37° C. overnight, and then centrifuged at 10,000 g for one minute to collect bacterial cells. From the bacterial cells thus collected, plasmids were recovered by use of the mini plus plasmid DNA extraction kit manufactured by Viogene. Elution was performed with 100 µl of EB. To 10 µl of an aliquot taken from the eluate, 3 µl of 10× Tango buffer, 1 µl of SacI (Fermentas), 1 µl of KpnI (Fermentas) and 15 µl of H$_2$O were added and reacted at 37° C. overnight. After completion of the reaction, extraction was performed with the equal amount of phenolic/chloroform/isoamyl alcohol. To the upper layer, 3 µl of 3 M sodium acetate was added, and 70 µl of cold ethanol was added. The mixture was allowed to stand still on ice for 5 minutes, and then centrifuged at 16,000 g and at 4° C. for 5 minutes to collect a precipitation. The precipitation was washed with 70% cold ethanol, and then dissolved in 40 µl of H$_2$O. To this, 5 µl of 10×BAP buffer (TOYOBO), and 5 µl of bacterial alkaline phosphatase (TOYOBO) were added. The reaction solution was reacted at 65° C. for one hour. The whole amount of reaction solution was subjected to 0.8% agarose electrophoresis with TAE buffer, and staining with an ethidium bromide solution was performed. After the position of a band was checked, the agarose gel was cut out. Recovery from the agarose gel was performed by use of the gel/PCR purification kit manufactured by Viogene. Elution was performed with 30 µl of EB in accordance with the accompanying protocol. The eluate was designated as vector solution 3.

The gene encoding EGFP was used as a template. 5'-CGAAGGTGAGCTCATGGTGAGCAAGGGCG-3' (primer 3: SEQ ID NO: 7) and 3'-AGACTGCGGTAC-CGATCGATCTGAGTCCG-3' (primer 4: SEQ ID NO: 8) were used as primers. Then, 20 µl of 5× PrimeStar buffer (TAKARA Bio), 1.0 µl of pET-EGFP, 0.5 µl of 100 µM primer 3, 0.5 µl of 100 µM primer 4, 8.0 µl of dNTP mix, 1.0 µl of PrimeStarHS, 20 µl of 5 M betain and 49 µl of H$_2$O were mixed, and subjected to the reaction consisting of 98° C., 2 min (the first step), 98° C., 10 sec (the second step), 55° C., 5 sec (the third step) and 72° C. and 90 sec (the fourth step), and a process from the second step to the fourth step was continuously repeated 35 times.

The resultant PCR fragments were purified by use of the gel/PCR purification kit manufactured by Viogene. Elution was performed with 50 µl of EB. To the aliquot (10 µl) of the resultant eluate, 3 µl of Tango buffer, 1 µl of SacI (Fermentas), 1 µl of KpnI (Fermentas) and 15 µl of H$_2$O were added, and a reaction was performed at 37° C. overnight. The whole amount of reaction solution was subjected to 0.8% agarose electrophoresis with TAE buffer and stained with an ethidium bromide solution. After the position of a band was checked, the agarose gel was cut out. Recovery from the agarose gel was performed by use of the gel/PCR purification kit manufactured by Viogene. Elution was performed with 30 µl of EB in accordance with the accompanying protocol. The eluate was designated as insert solution 3.

To 5 µl of vector solution 3 and 5 µl of insert solution 3, 10 µl of Ligation convenience solution was added. The reaction was performed at 16° C. for 30 minutes. After completion of the reaction, using the ligation solution, *Escherichia coli* DH5α was transformed. The resultant transformed strain was inoculated in 2 ml of LB medium sterilized by an autoclave and containing ampicillin, which was sterilized by a sterilized filter of 0.22 µm so as to obtain a final concentration of 100 µg/ml, cultured at 37° C. overnight, and then centrifuged at 10,000 g for one minute to collect bacterial cells. From the bacterial cells thus collected, plasmids were recovered by use of the mini plus plasmid DNA extraction kit manufactured by Viogene. Elution was performed with 100 µl of EB. Using the resultant eluate, *Escherichia coli* BLR strain (manufactured by Novagen) was transformed. The resultant transformed strain was designated as *E. coli* BLR/pCold2-EGFP-ColGCBD strain.

(2) Purification of EGFP-ColGCBD Culture

*Escherichia coli* BLR strain transformed with pCold2-EGFP-ColGCBD was inoculated in 2 ml of LB medium sterilized by an autoclave and containing ampicillin, which was sterilized by a sterilized filter of 0.22 µm so as to obtain a final concentration of 100 µg/ml, and cultured while shaking at 37° C. overnight. This was designated as a pre-culture solution. The pre-culture solution was inoculated to the same medium (170 ml) prepared in 500 ml-volume of a conical flask equipped with a baffle, so as to be an amount of 1/1000. Shaking culture was performed at 37° C. until OD$_{660}$ reached about 0.6 to 1.0. To this, IPTG sterilized by a sterilized filter of 0.22 µm was added so as to obtain a final concentration of 1 mM. The resultant mixture was cultured while shaking at 15° C. for 24 hours.

Recovery

After completion of the culture, bacterial cells were collected by centrifuge at 10,000 g for 5 minutes, suspended in a 50 mM phosphate buffer (pH 8.0) (the same amount as the culture solution) containing 0.3M NaCl, and collected again by centrifuge at 10,000 g for 5 minutes. The same operation was further repeated twice to wash the bacterial cells. The washed bacterial cells were suspended in 25 ml of the buffer, and then crushed by an ultrasonic homogenizer at a power of 200 W for one minute in ice. After completion of the crushing, the bacterial cells were centrifuged at 10,000 g for 10 minutes at 4° C., and the supernatant was collected.

Purification

Figure 1:
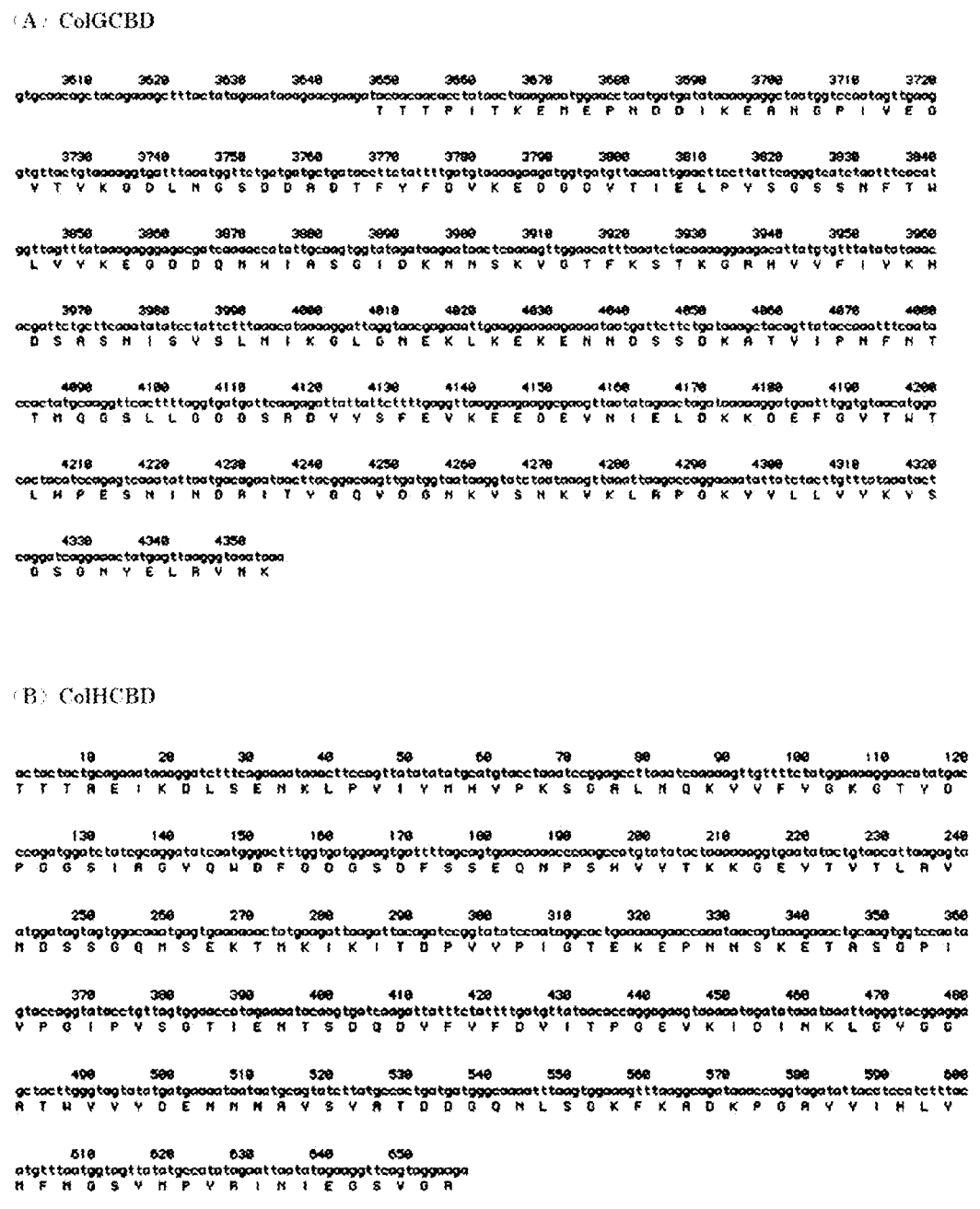

The supernatant centrifugally obtained from the crushed bacterial cells was subjected to Cosmosil His-accept (diameter: 2.5×10 cm) column chromatography. After the column was sufficiently washed with 50 mM phosphate buffer (pH 8.0) containing 0.3 M NaCl, a 50 mM phosphate buffer (pH 8.0) containing 10 mM imidazole and 0.3M NaCl was applied to the column in an equivalent amount to that of the column. Subsequently, the same buffer as above except that 20 mM imidazole was contained, the same buffer as above except that 30 mM imidazole was contained, the same buffer as above except that 40 mM imidazole was contained, the same buffer as above except that 50 mM imidazole was contained, the same buffer as above except that 100 mM imidazole was contained, and the same buffer as above except that 500 mM imidazole was contained, were applied, and the adsorbed protein was eluted. Individual elution fractions were checked by SDS-PAGE and immunoblot using an anti-His6 antibody (Santa Cruz). As a result, it was confirmed that a desired protein was contained in 20-30 mM imidazole elution fraction. This protein was designated as EGFP-ColGCBD protein. ColGCBD is shown in FIG. 1 (A), and the nucleotide sequence and amino acid sequence of EGFP-ColGCBD are shown respectively in SEQ ID NOs: 9 and 10 of the sequence listing.

Example 2

Preparation of Probes by Use of DsRed

[Preparation of DsRed-ColHCBD Probes]
(1) Method for Constructing DsRed-ColHCBD

Next, preparation of a probe (DsRed-ColHCBD) for *Clostridium histolyticum*-derived collagenase H labeled with DsRed will be described.

Based on the C-myc sequence, two oligo DNAs: 5'-TC-GACGAACAGAAACTGATTAGCGAAGAAGATCTGT-3' (SEQ ID NO: 11) and 5'-CTAGACAGATCTTCT-TCGCTAATCAGTTTCTGTTCG-3' (SEQ ID NO: 12) were synthesized. Each of the oligo DNAs was dissolved in TE so as to obtain a concentration of 100 μM. Then, 10 μl of oligo DNA, 3 μl of 10×T4 polynucleotide kinase buffer (Nippon Gene), 0.3 μl of 0.1 M ATP, 2 μl of T4 polynucleotide kinase (20 U, Nippon Gene) and 14.7 μl of $H_2O$ were mixed, and kept at 37° C. for one hour. An aliquot of 10 μl was taken from each of the reaction solutions, and the aliquots were mixed. The solution mixture was maintained at 100° C. for 5 minutes and directly cooled gradually to room temperature. This was designated as insert solution 4.

To 10 μl of pCold2 (TAKARA Bio), 10 μl of 10× Tango buffer (manufactured by Fermentas), 1 μl of SalI (Fermentas), 1 μl of XbaI (Fermentas) and 28 μl of $H_2O$ were added, and a reaction was carried out at 37° C. for 5 hours. After completion of the reaction, to the reaction solution, 150 μl of TE was added; further 250 μl of a phenolic/chloroform/isoamyl alcohol (25:24:1) solution was added, and sufficiently stirred. Thereafter, the mixture was centrifuged at room temperature for 5 minutes at 16,000 g, and the supernatant was collected. To the supernatant thus collected, 20 μl of a 3M sodium acetate solution was added, and 450 μl of cold ethanol was added. The mixture was allowed to stand still on ice for 5 minutes, and then centrifuged at 16,000 g and at 4° C. for 5 minutes to collect a precipitation.

The precipitation was washed with 70% cold ethanol, and then dissolved in 40 μl of $H_2O$. To this, 5 μl of 10×BAP buffer (manufactured by TOYOBO CO. LTD.) and 5 μl of bacterial alkaline phosphatase (TOYOBO) were added. A reaction was performed at 65° C. for one hour. The whole amount of reaction solution was subjected to 0.8% agarose electrophoresis. After completion of the electrophoresis, staining with an ethidium bromide solution was performed. After the position of a band was checked, the agarose gel was cut out. Recovery from the agarose gel was performed by use of the gel/PCR purification kit manufactured by Viogene. Elution was performed with 40 μl of EB in accordance with the accompanying protocol. The eluate thus obtained was designated as vector solution 4. Vector solution 4 (9 μl), 1 μl of insert solution 4 and 10 μl of Ligation convenience solution (Nippon gene) were mixed and kept at 16° C. for 30 minutes.

Using this solution, *Escherichia coli* DH5α was transformed. The *Escherichia coli* thus transformed was inoculated in 2 ml of LB medium sterilized by an autoclave and containing ampicillin, which was sterilized by a sterilized filter of 0.22 μm so as to obtain a final concentration of 100 μg/ml, cultured at 37° C. overnight, and then centrifuged at 10,000 g for one minute to collect bacterial cells. From the bacterial cells thus collected, plasmids were recovered by use of the mini plus plasmid DNA extraction kit manufactured by Viogene. Elution was performed with 100 μl of EB. To 10 μl of an aliquot taken from the eluate, 2 μl of 10×Tango buffer, 1 μl of XbaI and 7 μl of $H_2O$ were added and maintained at 37° C. for 3 hours. The reaction solution was subjected to 0.8% agarose gel electrophoresis, and a single band emerged in the vicinity of 4 kbp was cut out. Recovery was performed by use of the gel/PCR purification kit manufactured by Viogene. Elution was performed with 50 μl of EB. To 10 μl of the eluate, 10 μl of Ligation convenience solution was added and maintained at 16° C. for 30 minutes. Using the solution, *Escherichia coli* DH5α was transformed again. The *Escherichia coli* thus transformed was inoculated in 2 ml of LB medium sterilized by an autoclave and containing ampicillin, which was sterilized by a sterilized filter of 0.22 μm so as to obtain a final concentration of 100 μg/ml, cultured at 37° C. overnight, and then centrifuged at 10,000 g for one minute to collect bacterial cells. From the bacterial cells thus collected, plasmids were recovered by use of the mini plus plasmid DNA extraction kit manufactured by Viogene. Elution was performed with 100 ill of EB. To 10 μl of an aliquot taken from the eluate, 3 μl of 10×K buffer (TAKARA Bio), 1 μl of BamHI (TAKARA Bio), 1 μl of EcoRI (TAKARA Bio) and 15 μl of $H_2O$ were added and reacted at 37° C. overnight. After completion of the reaction, extraction was performed with the equal amount of phenol/chloroform/isoamyl alcohol. To the obtained upper layer, 3 μl of 3M sodium acetate was added, and 70 μl of cold ethanol was added. The mixture was allowed to stand still on ice for 5 minutes, and then centrifuged at 16,000 g and at 4° C. for 5 minutes to collect a precipitation. The precipitation was washed with 70% cold ethanol, and then dissolved in 40 μl of $H_2O$. To this, 5 μl of 10×BAP buffer (TOYOBO), and 5 μl of bacterial alkaline phosphatase (TOYOBO) were added. Reaction was performed at 65° C. for one hour. The whole amount of reaction solution was subjected to 0.8% agarose electrophoresis with TAE buffer, and staining with an ethidium bromide solution was performed. After the position of a band was checked, the agarose gel was cut out. Recovery from the agarose gel was performed by use of the gel/PCR purification kit manufactured by Viogene. Elution was performed with 30 µl of EB in accordance with the accompanying protocol. The resultant eluate was designated as vector solution 5.

In the meantime, 0.5 µl of 100 µM 5'-GAATCTTCAG-GATCCACTACTACTGCAGAAATAAAG-3' (primer 5: SEQ ID NO: 13) and 0.5 µl of 100 µM 5'-AAGCAGAGAT-GAATTCTCTTCCTACTGAACCTTCTATATTAATTC-3' (primer 6: SEQ ID NO: 14), 1 µl of a plasmid, pCold2-ColH-His, which had already been cloned and contained the whole length of a gene encoding *Clostridium histolyticum* collagnease H, 8 µl of dNTP mix (TAKARA Bio), 1.0 µl PrimeStar HS (TAKARA Bio), 20 µl of 5M betain and 49 µl of H$_2$O were mixed, and the reaction consisting of 98° C., 2 min (the first step), 98° C., 10 sec (the second step), 55° C., 5 sec (the third step) and 72° C. and 90 sec (the fourth step) was performed, and a process from the second step to the fourth step was continuously repeated 35 times.

The resultant PCR fragments were purified by use of the gel/PCR purification kit manufactured by Viogene. Elution was performed with 50 µl of EB. To the aliquot (10 µl) of the resultant eluate, 3 µl of 10×K buffer (TAKARA Bio), 1 µl of BamHI (TAKARA Bio), 1 µl of EcoRI (TAKARA Bio) and 15 µl of H$_2$O were added, and a reaction was performed at 37° C. overnight. The whole amount of reaction solution was subjected to 0.8% agarose electrophoresis with TAE buffer, and stained with an ethidium bromide solution. After the position of a band was checked, the agarose gel was cut out. Recovery from the agarose gel was performed by use of the gel/PCR purification kit manufactured by Viogene. Elution was performed with 30 µl of EB in accordance with the accompanying protocol. The eluate was designated as insert solution 5.

To 5 µl of vector solution 5 and 5 µl of insert solution 5, 10 µl of Ligation convenience solution was added. The reaction was performed at 16° C. for 30 minutes. After completion of the reaction, *Escherichia coli* DH5α was transformed by use of the ligation solution. The resultant transformed strain was inoculated in 2 ml of LB medium sterilized by an autoclave and containing ampicillin, which was sterilized by a sterilized filter of 0.22 µm so as to obtain a final concentration of 100 µg/ml, cultured at 37° C. overnight, and then centrifuged at 10,000 g for one minute to collect bacterial cells. From the bacterial cells thus collected, plasmids were recovered by use of the mini plus plasmid DNA extraction kit manufactured by Viogene. Elution was performed with 100 µl of EB. To 10 µl of an aliquot taken from this, 3 µl of 10×Tango buffer, 1 µl of SacI (Fermentas), 1 µl of KpnI (Fermentas) and 15 µl of H$_2$O were added and reacted at 37° C. overnight. After completion of the reaction, extraction was performed with the equal amount of phenolic/chloroform/isoamyl alcohol. To the obtained upper layer, 3 µl of 3 M sodium acetate was added, and 70 µl of cold ethanol was added. The mixture was allowed to stand still on ice for 5 minutes, and then centrifuged at 16,000 g and at 4° C. for 5 minutes to collect a precipitation. The precipitation was washed with 70% cold ethanol, and then dissolved in 40 µl of H$_2$O. To this, 5 µl of 10×BAP buffer (manufactured by TOYOBO CO., LTD.) and 5 µl of bacterial alkaline phosphatase (TOYOBO) were added. Reaction was performed at 65° C. for one hour. The whole amount of reaction solution was subjected to 0.8% agarose electrophoresis with TAE buffer, and staining with an ethidium bromide solution was performed. After the position of a band was checked, the agarose gel was cut out. Recovery from the agarose gel was performed by use of the gel/PCR purification kit manufactured by Viogene. Elution was performed with 30 µl of EB in accordance with the accompanying protocol. The eluate was designated as vector solution 6.

As a template, pDsRed-monomer (manufactured by Clontech) was used. 5'-GTACCGGTCGAGCTCATGGACAA-CACCGAGG-3' (primer 7: SEQ ID NO: 15) and 3'-GTCGCGGCCGGTACCCTGGGAGCCGGAGTGGC-3' (primer 8: SEQ ID NO: 16) were used as primers. Then, 20 µl of 5× PrimeStar buffer (TAKARA Bio), 1.0 µl of pDsRed-monomer (manufactured by Clontech), 0.5 µl of 100 µM primer 7, 0.5 µl of 100 µM primer 8, 8.0 µl of dNTP mix, 1.0 µl of PrimeStar HS, 20 µl of 5 M betain and 49 µl of H$_2$O were mixed, and subjected to the reaction consisting of 98° C., 2 min (the first step), 98° C., 10 sec (the second step), 55° C., 5 sec (the third step) and 72° C. and 90 sec (the fourth step) and a process from the second step to the fourth step was continuously repeated 35 times.

The resultant PCR fragments were purified by use of the gel/PCR purification kit manufactured by Viogene. Elution was performed with 50 µl of EB. To the aliquot (10 µl) of the resultant eluate, 3 µl of Tango buffer, 1 µl of SacI (Fermentas), 1 µl of KpnI (Fermentas) and 15 µl of H$_2$O were added, and a reaction was performed at 37° C. overnight. The whole amount of reaction solution was subjected to 0.8% agarose electrophoresis with TAE buffer, and stained with an ethidium bromide solution. After the position of a band was checked, the agarose gel was cut out. Recovery from the agarose gel was performed by use of the gel/PCR purification kit manufactured by Viogene. Elution was performed with 30 µl of EB in accordance with the accompanying protocol. The eluate was designated as insert solution 6.

To 5 µl of vector solution 6 and 5 µl of insert solution 6, 10 µl of Ligation convenience solution was added. The reaction was performed at 16° C. for 30 minutes. After completion of the reaction, *Escherichia coli* DH5α was transformed by use of the ligation solution. The resultant transformed strain was inoculated in 2 ml of LB medium sterilized by an autoclave and containing ampicillin, which was sterilized by a sterilized filter of 0.22 µm so as to obtain a final concentration of 100 µg/ml, cultured at 37° C. overnight, and then centrifuged at 10,000 g for one minute to collect bacterial cells. From the bacterial cells thus collected, plasmids were recovered by use of the mini plus plasmid DNA extraction kit manufactured by Viogene. Elution was performed with 100 µl of EB. Using the resultant eluate, *Escherichia coli* BLR (DE3) pLys strain (manufactured by Novagen) was transformed. The resultant transformed strain was designated as *E. coli* BLR/pCold2-DsRed-ColHCBD strain.

(2) Purification of DsRed-ColHCBD Culture

*Escherichia coli* BLR strain transformed with pCold2-DsRed-ColHCBD was inoculated in 2 ml of LB medium sterilized by an autoclave and containing ampicillin, which was sterilized by a sterilized filter of 0.25 µm so as to obtain a final concentration of 100 µg/ml, and cultured while shaking at 37° C. overnight. This was designated as a pre-culture solution. The pre-culture solution was inoculated to the same medium (170 ml) prepared in 500 ml-volume of a conical flask equipped with a baffle so as to be an amount of 1/1000. Shaking culture was performed at 37° C. until OD$_{660}$ reached about 0.6 to 1.0. To this, IPTG sterilized by a sterilized filter of 0.25 µm was added so as to obtain a final concentration of 1 mM. The resultant mixture was cultured while shaking at 15° C. for 24 hours.

Recovery

After completion of the culture, bacterial cells were collected by centrifuge at 10,000 g for 5 minutes, suspended in a 50 mM phosphate buffer (pH 8.0) (the same amount as the culture solution) containing 0.3M NaCl, and collected again by centrifuge at 10,000 g for 5 minutes. The same operation was repeated further twice to wash the bacterial cells. The washed bacterial cells were suspended in 25 ml of the buffer, and then crushed by an ultrasonic homogenizer at a power of 200 W for one minute in ice. After completion of the crushing, the bacterial cells were centrifuged at 10,000 g for 10 minutes at 4° C., and the supernatant was collected.

Purification

The supernatant centrifugally obtained from the crushed bacterial cells was subjected to Cosmosil His-accept (diameter: 2.5×10 cm) column chromatography. After the column was sufficiently washed with 50 mM phosphate buffer (pH 8.0) containing 0.3 M NaCl, a 50 mM phosphate buffer (pH 8.0) containing 10 mM imidazole and 0.3M NaCl was applied to the column in an equivalent amount to that of the column. Subsequently, the same buffer as above except that 20 mM imidazole was contained, the same buffer as above except that 30 mM imidazole was contained, the same buffer as above except that 40 mM imidazole was contained, the same buffer as above except that 50 mM imidazole was contained, the same buffer as above except that 100 mM imidazole was contained, and the same buffer as above except that 500 mM imidazole was contained, were applied, and the adsorbed protein was eluted. Individual elution fractions were checked by SDS-PAGE and immunoblot using an anti-His6 antibody (Santa Cruz). As a result, it was confirmed that a desired protein was contained in 20-30 mM imidazole elution fraction. This protein was designated as DsRed-ColHCBD protein. ColHCBD is shown in FIG. 1 (B), and the nucleotide sequence and amino acid sequence of DsRed-ColHCBD are shown respectively in SEQ ID NOs: 17 and 18 of the sequence listing.

Example 3

Preparation of Probes by Use of tdTomato (1) Preparation of tdTomatoColH CBD DNA and Insertion into Expression Vector pColdII As template DNA of tdTomato gene, ptdTomato vector (Clontech) was used. In PCR for DNA amplification, as an N-terminal primer, sequence 34 base (TomatoF) containing an Nde I recognition site positioned upstream of tdTomato was used. As a C-terminal primer, a complementary sequence to 34 bp (TomatoR) having a BamHI recognition site in place of a termination codon positioned downstream of tdTomato was used. The sequences of individual primers are shown below.

Primer sequence:

```
TomatoF:
                                      (SEQ ID NO: 19)
5'-CCGGTCGCCcatATGGTGAGCAAGGGCGAGGAGG-3'

TomatoR:
                                      (SEQ ID NO: 20)
5'-AGAGTCGCGGCGGATCCCTTGTACAGCTCGTCCA-3'
```

Subsequently, pCold II having an insert of DsRed-ColH CBD DNA was treated with restriction enzymes, BamH I and Xba I, to obtain a Col H CBD DNA fragment of about 1000 bp.

tdTomato DNA of about 1500 bp prepared by PCR was treated with Nde I and BamHI and inserted together with ColH CBD DNA into expression vector pCold II treated with Nde I, Xba I. Colony PCR and sequence data analysis were performed to confirm that a plasmid is constructed as designed. Note that DNA sequence analysis was asked to Operon Biotechnologies. When tdTomatoColH CBD DNA was inserted into pCold II, it was expressed as a protein having a His-tag sequence at the N-terminal (FIG. 2). The residues of designed tdTomatoColH CBD including these amino acid sequences becomes 726 (molecule amount 82 k).

(2) Preparation of Expression Bacteria and Induction of Protein Expression

*Escherichia coli* BLR was transformed with the tdTomatoColH CBD expression plasmid constructed in the aforementioned method. A general heat shock method was used for transformation. The transformed *Escherichia coli* BLR was spread on an LB plate containing 100 µg/ml ampicillin (Amp) and cultured at 37° C. overnight. The grown colonies were subcultured onto an LB/Amp liquid medium and incubated at 37° C. until $OD_{600}$ reached 0.5-0.7. The culture solution was cooled on ice for 30 minutes, and then isopropyl-β-D-thiogalactopyranoside (IPTG) was added so as to obtain a concentration of 0.1 mM. Culture was continued at 15° C. for 24 hours to induce expression of a protein.

After 24 hours, the *Escherichia coli* culture solution was centrifuged to collect bacterial cells. The bacterial cells were washed with phosphate buffered saline (PBS) twice, and again suspended in PBS. To this, phenylmethanesulphonyl fluoride (PMSF) was added so as to obtain a concentration of 0.1 mM. The bacterial cells were crushed by ultrasonic wave while cooling on ice. The resultant solution of crushed bacterial cells was centrifuged at 12,000 rpm for 20 minutes to separate a precipitation and a supernatant. SDS-PAGE analysis was performed to confirm that a desired protein is expressed in a soluble fraction. To *Escherichia coli* cultured solution, dimethyl sulfoxide (DMSO) was added up to 8% and stored at −80° C. in a freezer. This was used as a frozen bacterial-cell stock for expressing tdTomatoColH CBD.

(3) Purification of tdTomatoColH CBD

Figure 3:
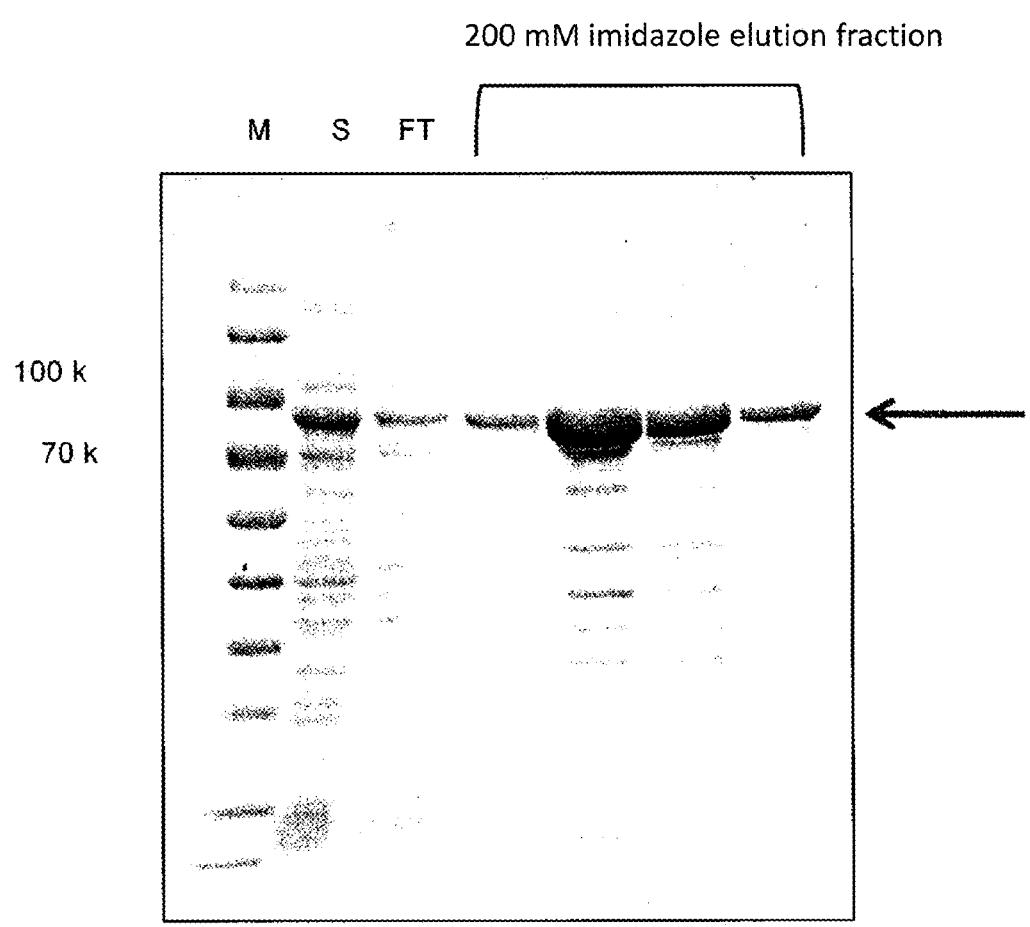
FIG. 3 shows SDS-PAGE of Ni-NTA elution fraction.

To Ni-NTA agarose column ((φ2.0 cm×5.0 cm, column volume 15 ml, company: QIAGEN) equilibrated with a 300 mM NaCl/50 mM sodium phosphate buffer (pH 8.0), a solution prepared by diluting the soluble fraction of crushed bacterial cells three-fold with an equilibration buffer was applied. After the flow-through fraction not adsorbed to the carrier was washed off with the equilibration buffer, elution was performed with buffers containing 50 mM, 200 mM, and 500 mM imidazole. Each of the fractions eluted by the buffers different in imidazole concentration was subjected to SDS-PAGE to confirm that tdTomatoColH CBD was eluted in a 200 mM imidazole elution fraction (FIG. 3). The fraction was recovered and dialyzed against 50 mM Tris-HCl (pH 8.0).

Figure 4:
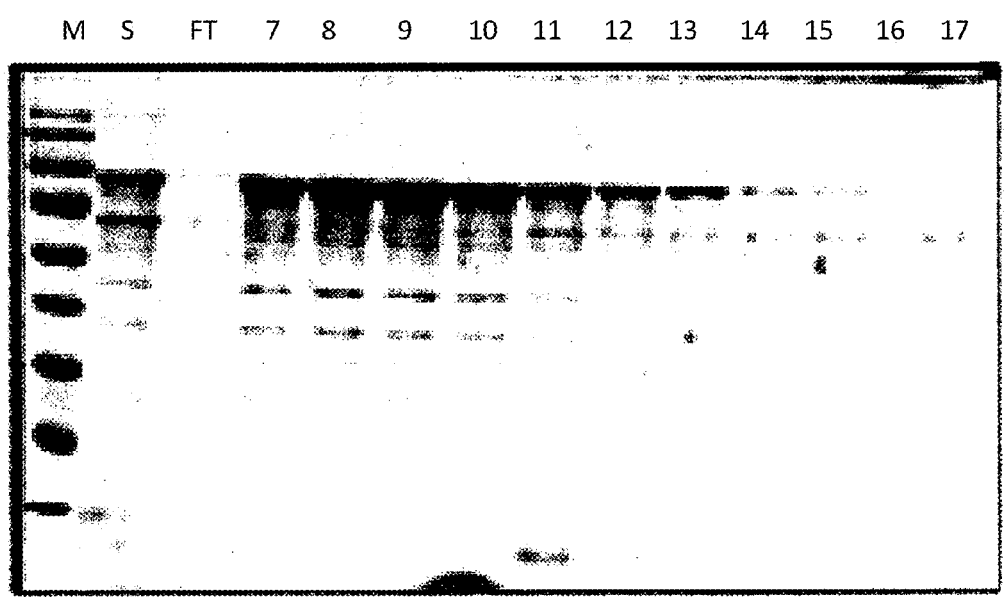
FIG. 4 shows SDS-PAGE of anionic exchange chromatography elution fraction.

After the dialysis, the resultant solution was applied to an anionic exchange column (HiTrap DEAE FF, C.V.=1 ml, GE Healthcare), and elution was performed with the 0-400 mM linear NaCl concentration gradient. A fraction in which the presence of tdTomatoColH CBD was confirmed by SDS-PAGE was recovered from the elution fractions (FIG. 4), and concentrated by ultrafiltration using Amicon 30k (manufactured by Millipore) up to 5 mg/ml. This was used as purified tdTomatoColH CBD.

(4) Measurement of Fluorescent Spectrum

Figure 5:
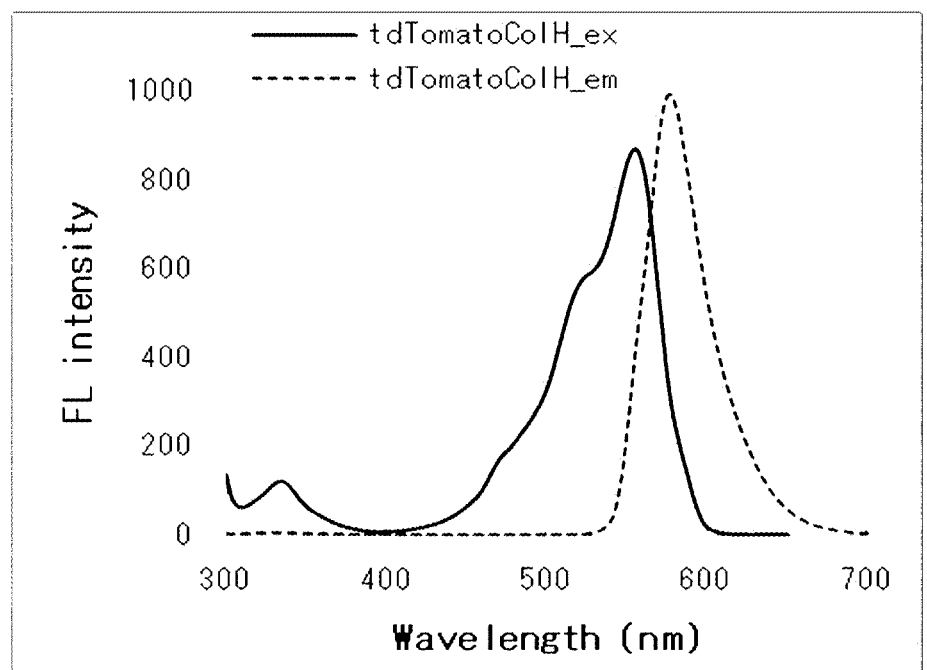
FIG. 5 shows excitation and fluorescent spectra of tdTomatoColH CBD.

It is reported that tdTomato has the same excitation wavelength (554 nm) and fluorescent (581 nm) wavelength as those of DsRed. The excitation and fluorescent spectrum of the tdTomatoColH CBD purified enzyme solution was measured by a spectrofluorometer F-2500 (Hitachi High-Technologies Corporation) (FIG. 5). From the spectrum, it was confirmed that neither a shift of a fluorescent wavelength nor quenching occur by being expressed as a fusion protein with CBD. Furthermore, it was confirmed that more intensive fluorescence is emitted compared to that using DsRed.

Example 4

Preparation of Probe Using Luciferase

[Method for Preparing PGV_Col G CBD and PGV-Col H CBD (Luciferase-Collagen Binding Domain Fusion Protein) Probes]
(1) Method for Constructing PGV_Col G CBD
1) Preparation of DNA of Luciferase-Collagen Binding Domain Fusion Protein
Insertion into Expression Vector pCold I
As a template DNA of a Luciferase gene, the sequence of a luciferase coding region (PGV) of a PicaGene control vector (PGV control) was used. In PCR for DNA amplification, as an N-terminal primer, a 27-base sequence (PGVctrl_Nterm) having an Nde I recognition site (CATATG) positioned upstream of PGV was used. As a C-terminal primer, a 30 bp (PGV_CF_r) sequence complementary to a BamHI recognition site (GGATCC) positioned downstream of PGV in place of a termination codon was used.

Figure 6:
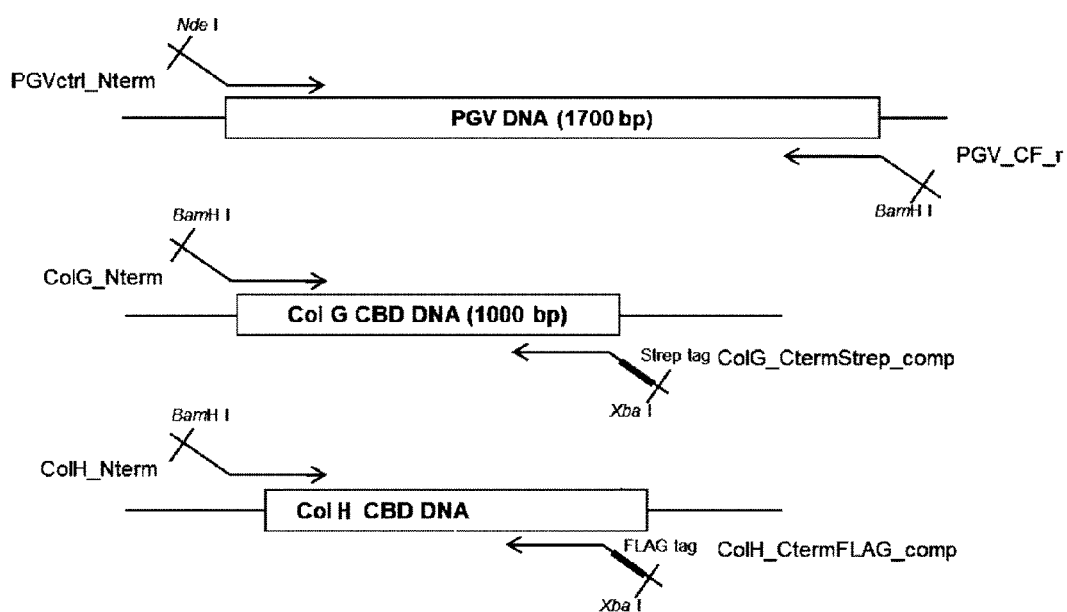
FIG. 6 shows schematic views of the primers used for amplification of a luciferase gene and a CBD gene.

For collagen binding domains (CBD) of Collagenases (Col) G and H, a plasmid having the whole length DNA of Col G and H inserted in pCold III was used as template DNA. In PCR for DNA amplification, a 35-base (ColG_Nterm, ColH_Nterm) DNA having a BamH I recognition site added to the N-terminal of CBD was used as an N-terminal primer. As a C-terminal primer, a sequence (ColG_CtermStrep_comp) in which a Strep-tagged amino acid sequence and an Xba I recognition site (TCTAGA) were added sequentially in this order to Col G CBD, and a complementary 49-base DNA to the sequence (ColH_CtermFLAG_comp) in which FLAG-tagged amino acid sequence and an Xba I recognition site were sequentially added in this order to Col H CBD were respectively used (FIG. 6).

Figure 7:
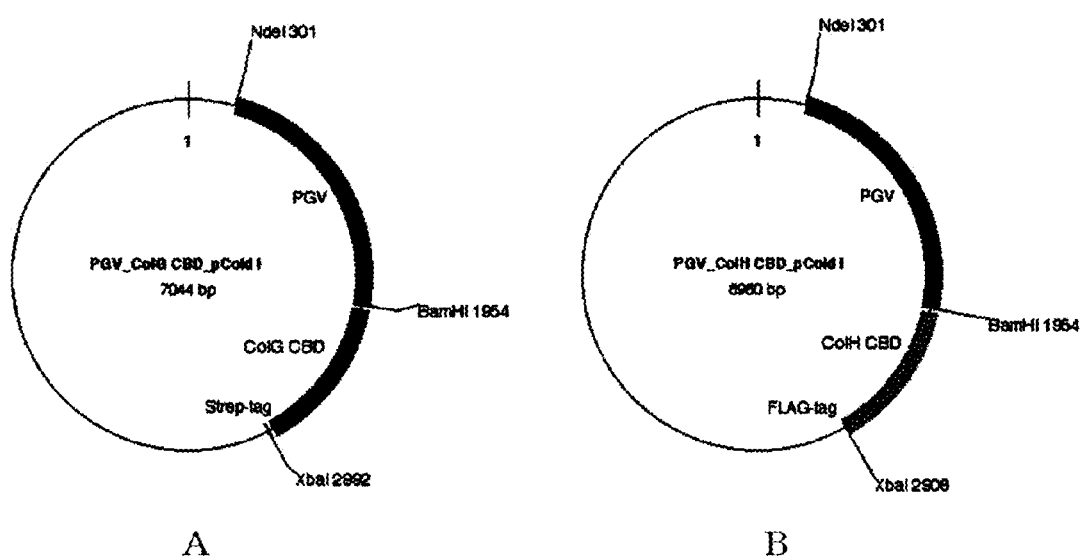
FIG. 7 shows luciferase-collagen binding domain fusion protein expression plasmids.

PGV DNA of about 1,700 bp prepared by PCR was treated with Nde I and BamHI, and CBD DNA of about 1,000 bp was treated with BamH I and Xba I, and inserted into an expression vector, pCold I that had been treated with Nde I and Xba I (FIG. 7).

Colony PCR and sequence data analysis were performed to confirm that the plasmid was constructed as designed. Note that DNA sequence analysis was asked to Operon Biotechnologies. If DNA was inserted into pCold I, it was expressed as a protein having His-tag at the N-terminal and a recognition sequence for Factor Xa. The size of the fusion protein designed including these amino acid sequences becomes 911 residues (molecule amount: 101 k) in the case of PGV Col G CBD and 883 residues (molecule amount: 98 k) in the case of PGV Col H CBD.

2) Preparation of Expression Bacteria and Induction of Protein Expression

*Escherichia coli* Rosetta 2 (DE3) was transformed with the expression plasmid in which PGV and DNA of Col G CBD or Col H CBD were inserted. A general heat shock method was used for transformation. Expression of a Luciferase-Collagen binding domain fusion protein was induced by the transformed strain.

The transformed *Escherichia coli* Rosetta 2 was spread on an LB plate containing 100 μg/ml of ampicillin (Amp) and 34 μg/ml of chloramphenicol (Cm) and cultured at 37° C. overnight. Grown colonies were subcultured onto an LB/Amp/Cm liquid medium and incubated at 37° C. until $OD_{600}$ reached 0.5-0.7. The culture solution was cooled on ice for 30 minutes, and then isopropyl-β-D-thiogalactopyranoside (IPTG) was added so as to obtain a concentration of 0.1 mM. Culture was continued at 15° C. for 48 hours to induce expression of a protein.

Figure 8:
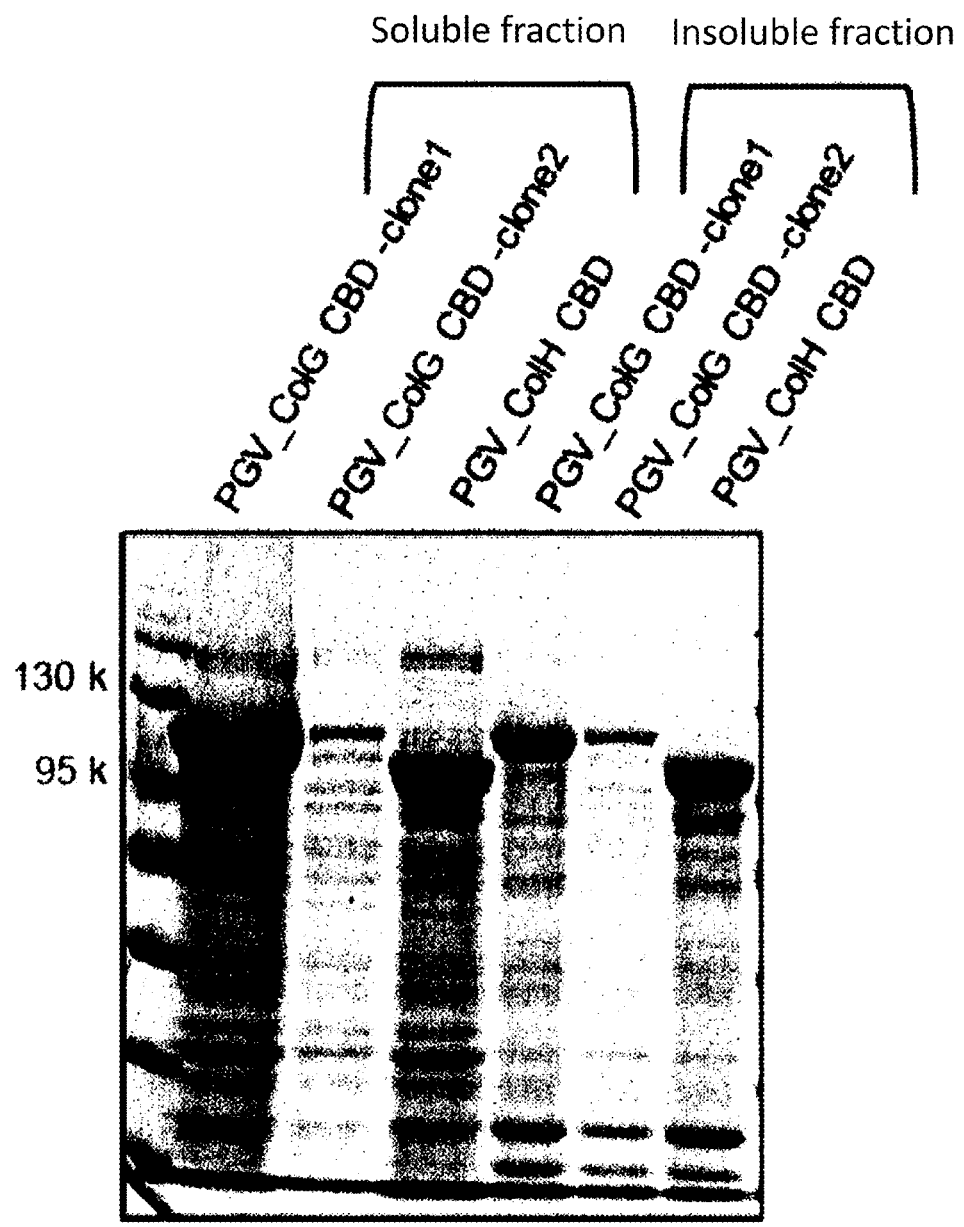
FIG. 8 shows detection of expression of probe protein (SDS-PAGE).

After 48 hours, the *Escherichia coli* culture solution was centrifuged to collect bacterial cells. The bacterial cells were washed with phosphate buffered saline (PBS) twice and again suspended in PBS. To this, phenylmethanesulphonyl fluoride (PMSF) was added so as to obtain a concentration of 0.1 mM. Thereafter, the bacterial cells were crushed by ultrasonic wave under conditions: the maximum power, 2 sec interval pulse, and for 15 minutes. The resultant solution of crushed bacterial cells was centrifuged at 12,000 rpm for 20 minutes to separate a precipitation and a supernatant. SDS-PAGE analysis was performed to confirm expression of a protein. As a result of SDS-PAGE, bands of proteins having sizes presumably corresponding to PGV_Col G CBD (101 k) and PGV_Col H CBD (98 k) were detected (FIG. 8). These bands were also detected by Western blot using an anti-His-tag antibody. To the *Escherichia coli* cultured solution in which a desired protein was confirmed to be expressed, dimethyl sulfoxide (DMSO) was added up to 8% and stored at −80° C. in a freezer. This was used as a frozen bacterial-cell stock of PGV_Col G CBD or PGV_Col H CBD.

3) Determination of Luciferase Activity

Figure 9:
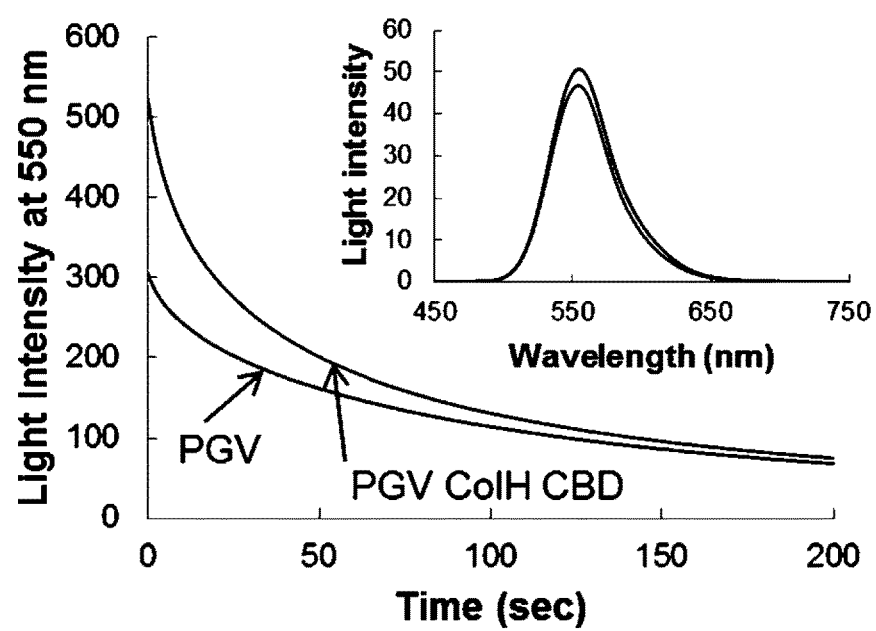
FIG. 9 shows the detection of luciferase luminescence (luminescent spectrum and a change of light intensity at 550 nm with time).

In the supernatant obtained after bacterial cells of transformed strain were crushed, the presence of a protein having a luciferase activity was confirmed. Luciferase used in the present invention has a luminescent spectrum having a maximum value at 550 nm. After 50 mM Tris-HCl (pH 8.0) was mixed with the crude, a substrate solution (Tripluc Luciferase Assay Reagent, TOYOBO CO., LTD.) was added. Immediately after, luminescence at 550 nm was measured with the passage of time. The luminescence of luciferase reached maximum immediately after a substrate solution was added, and thereafter decreased. Measurement was continued until luminescence decreased and apparently reached almost a plateau. Thereafter, a luminescent spectrum was measured (FIG. 9). Also when a fusion protein with CBD was expressed, the same luminescence as that of single PGV was shown. In the crude obtained immediately after crushing, intensive luminescence was observed at 550 nm. In the case of the crude stored in a freezer at −80° C., it was confirmed that luminescence gradually decreased and that inactivation was more suppressed compared to crudes stored at 4° C. and −20° C.

(2) Purification Method

Figure 10:
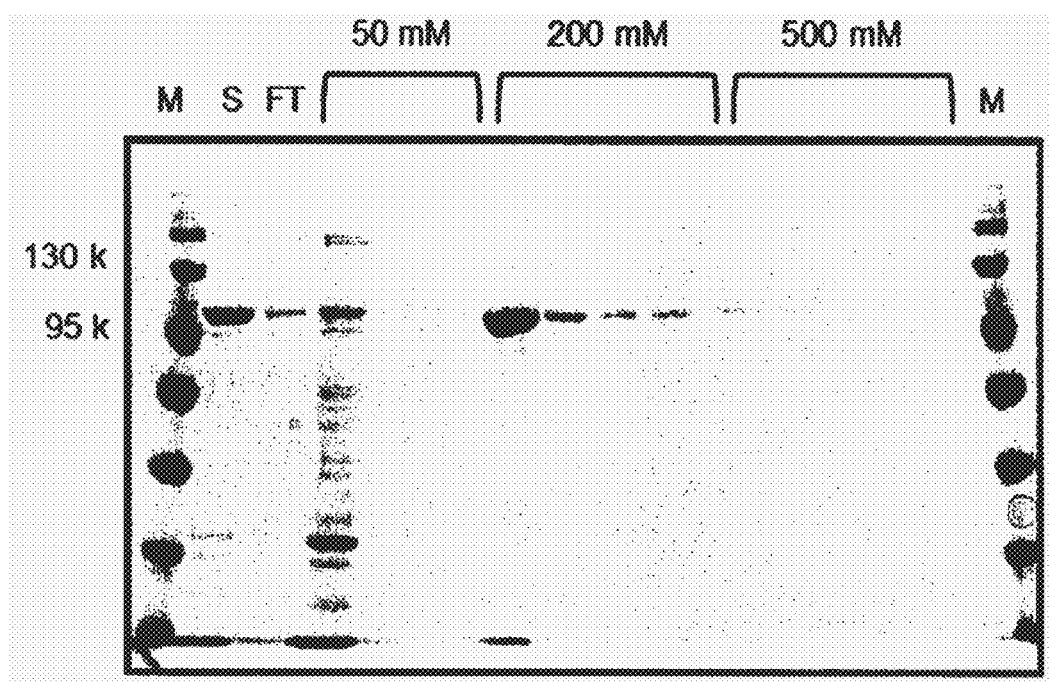
FIG. 10 shows SDS-PAGE of Ni-NTA agarose column elution fraction (M: Protein marker, S: PGV_ColH CBD crude, FT: flow-through fraction, 50 to 500 mM: imidazole elution fraction at individual concentrations (the first 200-mM imidazole elution fraction was used as purified enzyme solution)).

To an Ni-NTA agarose column (diameter: 2.0 cm×5.0 cm, column volume 15 ml, QIAGEN) equilibrated with a 300 mM NaCl/50 mM sodium phosphate buffer (pH 8.0), a solution, which was prepared by diluting the crude (obtained after bacterial cells were crushed) 10-fold with an equilibration buffer, was applied. After the flow-through fraction not adsorbed to the carrier was washed off with the equilibration buffer, elution was performed with buffers containing 50 mM, 200 mM, and 500 mM imidazole. Each of the fractions eluted by the buffers different in imidazole concentration was checked by SDS-PAGE. A 200 mM-imidazole elution fraction was determined as a fraction containing purified PGV_ColG CBD or PGV_ColH CBD (FIG. 10).

Example 5

Determination of Binding to Pancreatic Tissue

Figure 11:
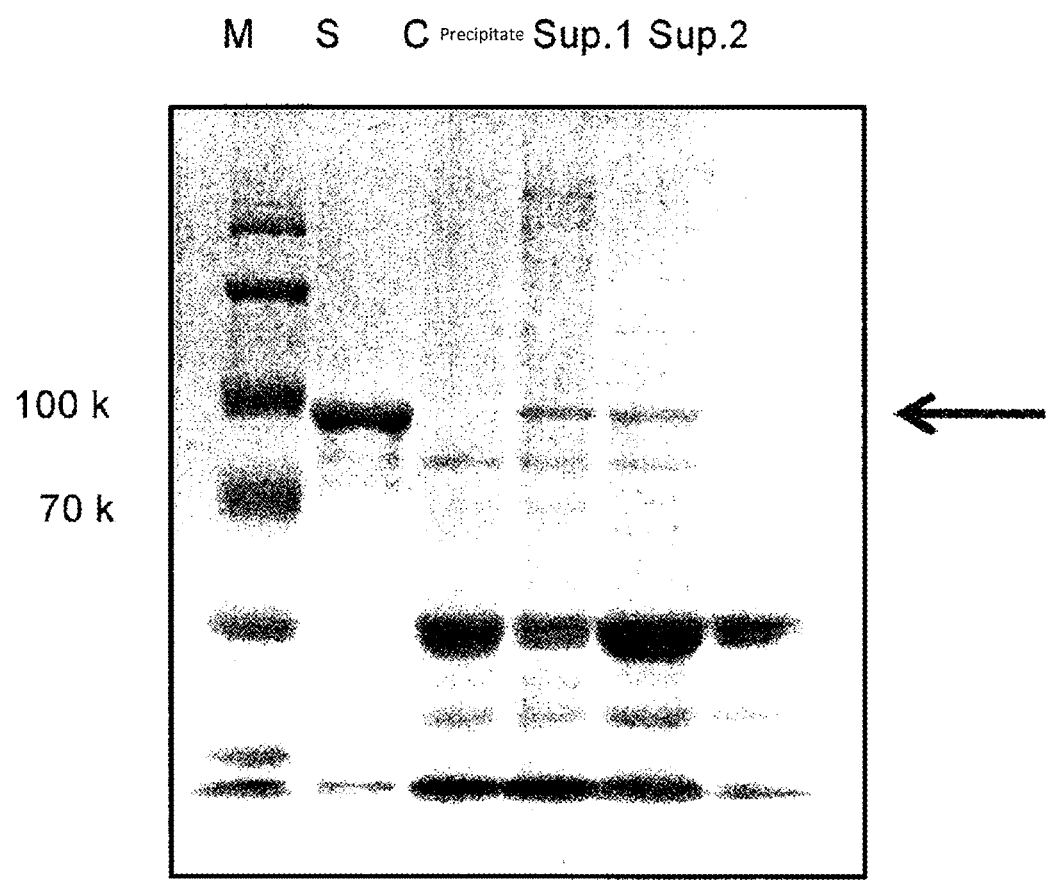
FIG. 11 shows a confirmation experiment for binding to a pancreatic tissue piece.

Swine pancreatic tissue pieces suspended in 100 μl of 50 mM Tris-HCl/5 mM $CaCl_2$ (pH 7.5) were mixed with a purified enzyme solution (100 μl) and incubated at 37° C. for 30 minutes, and then centrifuged to separate a precipitation and a supernatant (sup.1). The resultant precipitation was suspended in a 50 mM acetic acid buffer (pH 5.0) and incubated at room temperature for 20 minutes, and then centrifuged to separate a precipitation and a supernatant (sup.2). The resultant precipitation and the supernatant were subjected to SDS-PAGE to check binding of the pancreatic tissue to tdTomato-ColH CBD (FIG. 11).

As a results of SDS-PAGE, a band of tdTomatoColH CBD was observed in the precipitation. From this, binding to the pancreatic tissue was confirmed. It was found that tdTomatoColH CBD bound to the pancreatic tissue was fractionated into a precipitation and tdTomatoColH CBD unbound was fractionated into sup.1. Furthermore, since no band was detected in sup.2, it was found that tdTomatoColH CBD still binds to a collagen fiber under acidic pH conditions.

Example 6

Method for Analyzing a Biological Tissue Component Using Probe

[Method for Measuring a Biological Component]

A method for measuring a biological component of the present invention will be described.

(1) Method for Measuring a Biological Component by EGFP-ColGCBD and DsRED-ColH

From a pig died of blood removal, the pancreas was excised out and cut into pieces of 5 mm$^2$. The pancreas pieces each were embedded in the OCT compound (manufactured by Sakura Finetek Co., Ltd.) and frozen by liquid nitrogen. Thereafter, the pancreas piece was sliced into thin pieces of 8 μm in thickness by Cryostat CM 3050S (manufactured by Leica). Each of the thin pieces was attached onto the slides (manufactured by Matsunami Glass Ind., Ltd.). The prepared slide was soaked in a formalin solution (manufactured by WAKO), the concentration of which was controlled to be 10% with a phosphate buffer solution (PBS (−)) containing neither calcium ion nor magnesium ion, and incubated at room temperature for 10 minutes, and then dried for 30 minutes. To a glass cuvette, PBS (−) was poured, and the slide was incubated in the cuvette for 5 minutes at room temperature. The prepared slide was stored in a moisture box such that the slide would not be dried. The prepared slide was soaked in an EGFP-ColGCBD solution (200 μl) and incubated at 37° C. for one hour. After completion of the incubation, washing was performed with PBS (−) for 5 minutes. The prepared slide was washed with PBS (−) in a washing bottle and covered with VECTORSHELD (manufactured by Vector). Thereafter, the prepared slide was observed by a fluorescent microscope BIOLEVO BZ 9000 (manufactured by KEYENCE CORPORATION), and an image was photographed.

(2) Measurement Results

Figure 12:
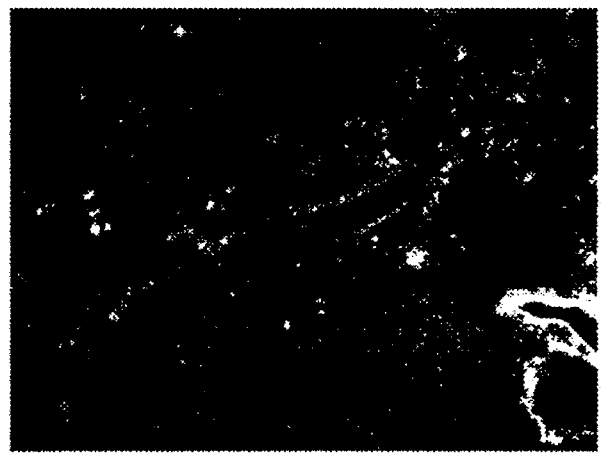
FIG. 12 shows the results of component analysis of a swine pancreatic piece by EGFP-ColGCBD probe.
Figure 12:
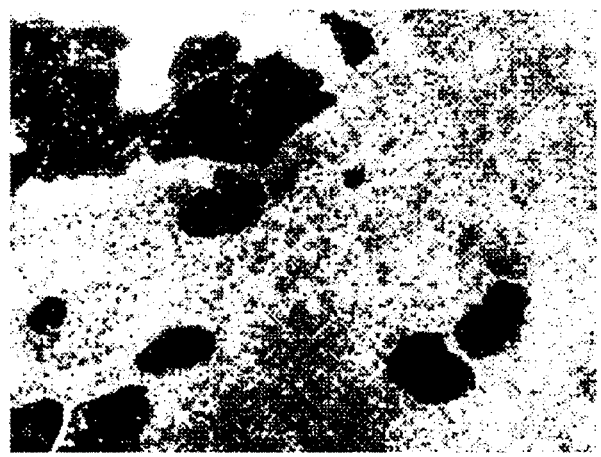

The results are shown in FIG. 12. Compared to a negative control, in the tissue sample stained by EGFP-ColGCBD, the region where the tissue is present was satisfactorily stained.

Example 7

Method for Measuring Tissue Piece (1) Observation Method

A prepared slide on which the rat's pancreatic tissue piece was fixed and stored at −80° C. was soaked in 5 mM CaCl$_2$/TBS at room temperature for 10 minutes and washed with Milli-Q. To block a nonspecific binding, 100 μl of 2% Myoglobin (Myb) was added dropwise to the prepared slide, which was then pre-incubated at 37° C. for 30 minutes, and then washed with Milli-Q. Each of the protein (GFP control, GFP ColG CBD, tdTomato control, tdTomatoColH CBD) solutions (40 μl) and 2% Myb (40 μl) were mixed. Then, each of the mixtures was added dropwise onto the tissue pieces and incubated 37° C. for 30 minutes. The concentrations of the protein solutions were controlled as follows: GFP control: 10 mg/ml, GFP ColG CBD: 10 mg/ml, tdTomato control: 5 mg/ml, tdTomatoColH CBD: 5 mg/ml.

The prepared slide was soaked in 5 mM CaCl$_2$/TBS at room temperature for 10 minutes and washed with Milli-Q.

After this procedure was repeated twice, the prepared slide was observed by a fluorescent microscope BIOREVO BZ-9000 (manufactured by KEYENCE CORPORATION) at a magnification of 200×. Several regions were appropriately selected and images were photographed at an exposure time of 0.5 seconds.

Using gauging function of software attached to the microscope, a histogram of the brightness of the entire photograph was prepared. In GFP control and GFP ColG CBD, the brightness of green fluorescence alone was selected, whereas in tdTomato control and tdTomatoColH CBD, the brightness of red fluorescence alone was selected.

From the histogram, differences of average brightness value (delta average brightness) between GFP control and GFP ColG CBD, and between tdTomato control and tdTomatoColH CBD was calculated and organized for each lineage. As a value of delta average brightness thus calculated increases, the number of bonds between CBD and the tissue increases, indicating that fluorescent intensity significantly differs from the control. As a result that the delta average brightness values were compared with each other, binding of ColG CBD and ColH CBD to the pancreatic tissue differs depending upon the lineage and age in week.

(2) Method for Separating Rat Pancreatic Islet

Based on "Guide for the Care and Use of Laboratory Animals (revised in 1996)" published by the National Institutes of Health of the United States, animal experiments were carried out. Male Lewis rats (Slc, Japan) having a body weight of 239-268 g, male SD rats (Slc, Japan) having a body weight of 255-301 g and male Wistar-Furth rats (Slc, Japan) having a body weight of 197-231 g were used.

Experimental groups were set without changing the amount of Thermolysin (0.322 mg) serving as a neutral protease as follows: a group providing a recombinant-type high-purity product: Col G (5.46 mg) and Col H (2.02 mg) in a standard enzyme-amount ratio of (H/G ratio) of 3.7; a 10-fold group (Col G (4.96 mg), Col H (18.34 mg), Thermolysin (0.322 mg), (H/G ratio=3.70)); a 1/10 fold group (Col G (5.51 mg), Col H (0.20 mg), Thermolysin (0.322 mg), (H/G ratio=0.04)); a Col G complete-absent group, and a Col H complete-absent group. Before the pancreas was excised out, enzyme combinations solved in cold Hanks' Balanced Salt Solution (HBSS) were injected through the ductus cboledochus to expand the pancreatic tissues. After 10 mL of HBSS was added, the pancreas was placed in a warm bath of 37° C. or less for 14 minutes to digest it. Subsequently, concentration-gradient centrifugation using Histopaque-1119 (Sigma Diagnostics, St. Louis, Mo., USA) and Lymphoprep™ (NycomedPharma AS, Oslo, Norway) was carried out to take a layer containing pancreatic islets. The tissue obtained by the pancreatic islet separation operation was stained with diphenylthiocarbazone (Wako, Osaka, Japan) to distinguish the pancreatic islets from non-pancreatic islet tissue such as an exocrine gland and an excreting duct. Each yield was measured directly under microscopic observation. The yield of separated pancreatic islets was indicated in terms of islet equivalent (IEQ) (1 IEQ corresponds to the size of a pancreatic islet of 150 μm in diameter. This is defined by the international standard).

(3) Experimental Results

Figure 13:
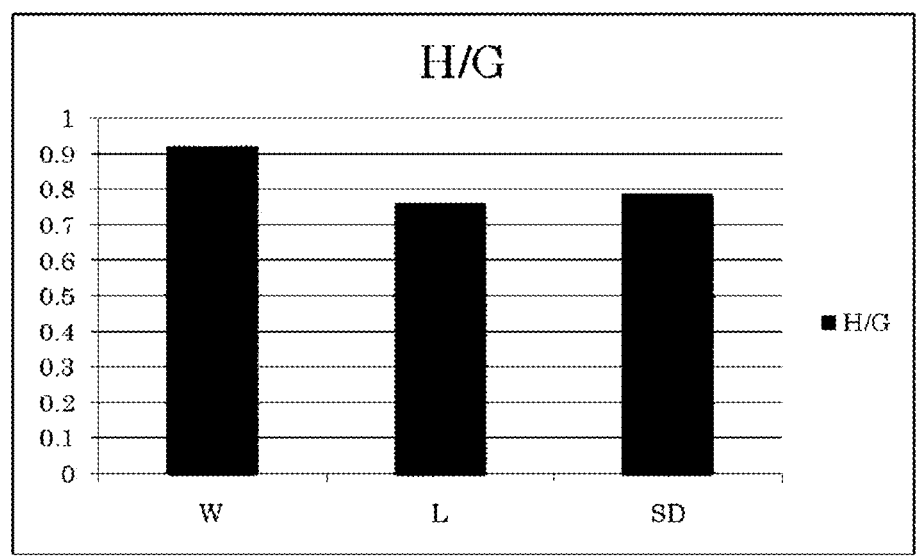
FIG. 13 shows a fluorescent brightness ratio of GFP ColG CBD and tdTomato ColH CBD in a rat tissue piece (H/G: fluorescent brightness ratio of tdTomato ColH CBD relative to GFP ColG CBD, W: Wister-Furth rat, L: Lewis rat, SD: SD rat).

1) Measurement Results of Fluorescent Brightness of GFP ColG CBD and tdTomatoColH CBD in Tissue Pieces of Rats The fluorescent brightness of two probes, i.e., ColG and ColH in rats and the ratio of them are shown in FIG. 13 and Table 1.

TABLE 1

| Rat | Probes | | Fluorescent brightness | | | |
|---|---|---|---|---|---|---|
| | | | Sample ① | Sample ② | Sample ③ | Sample ④ |
| Wister | G | Compartment ① | 74 | 109 | 78 | — |
| | | Compartment ② | 89 | 114 | 87 | — |
| | | Compartment ③ | 80 | 127 | 73 | — |
| | | Compartment ④ | — | 105 | 73 | — |
| | | Average value | 81 | 109 | 78 | — |
| | H | Compartment ① | 76 | 125 | 65 | — |
| | | Compartment ② | 70 | 118 | 71 | — |
| | | Compartment ③ | 68 | 101 | 80 | — |
| | | Compartment ④ | — | 105 | 64 | — |
| | | Average value | 71 | 108 | 70 | — |
| | H/G | | 0.881 | 0.991 | 0.897 | — |
| Lewis | G | Compartment ① | 79 | 88 | 95 | 70 |
| | | Compartment ② | 84 | 97 | 106 | 77 |
| | | Compartment ③ | 80 | 79 | 125 | 71 |
| | | Compartment ④ | — | 90 | 104 | 82 |
| | | Average value | 81 | 89 | 108 | 75 |
| | H | Compartment ① | 62 | 66 | 106 | 57 |
| | | Compartment ② | 60 | 64 | 93 | 58 |
| | | Compartment ③ | 61 | 57 | 91 | 60 |
| | | Compartment ④ | — | 67 | 76 | 74 |
| | | Average value | 61 | 64 | 87 | 58 |
| | H/G | | 0.753 | 0.719 | 0.806 | 0.773 |
| SD | G | Compartment ① | 85 | 115 | 84 | — |
| | | Compartment ② | 83 | 109 | 72 | — |
| | | Compartment ③ | 87 | 121 | 72 | — |
| | | Compartment ④ | — | 135 | 78 | — |
| | | Average value | 85 | 120 | 77 | — |
| | H | Compartment ① | 68 | 77 | 56 | — |
| | | Compartment ② | 71 | 106 | 55 | — |
| | | Compartment ③ | 69 | 113 | 46 | — |
| | | Compartment ④ | — | 85 | 61 | — |
| | | Average value | 69 | 101 | 55 | — |
| | H/G | | 0.816 | 0.842 | 0.714 | — |

2) Pancreatic Islet Separation Results in Rats

In the case where the fluorescent-brightness ratio of two probes, ColG and ColH, i.e., an H/G value is 0.85 or more, the addition-amount ratio of ColH to ColG, i.e., ColH/G ratio, must be an optimal value. However, in the case where the H/G value is 0.8 or less, the ColH/G ratio does not have a significant effect. It was found that if ColG is not added, the yield of a pancreatic islet is not significantly affected. A pancreatic islet separation test was performed by changing the content ratio of ColH and ColG to be used for separation of pancreatic inlets in rats in accordance with the aforementioned numerical value. The yield of pancreatic islets in this test was measured. The results are shown in Table 2.

TABLE 2

| Yield of pancreatic islet (IEQ) | Lewis | SD | Wistar |
|---|---|---|---|
| In the case of ColH/ColG = 2/10 (standard value) | | | |
| | 2772 | 2836 | 3050 |
| | 3040 | 3104 | 2224 |
| | 3806 | 2516 | 2927 |
| Average value | 3206 | 2819 | 2734 |
| In the case of ColH/ColG = 1/10 | | | |
| | 2049 | 1855 | 1306 |
| | 2827 | 2669 | 1174 |
| | 2710 | 2311 | 1997 |
| | 2748 | 2220 | 1493 |
| | 2752 | 1747 | |
| | 3404 | 3541 | |
| Average value | 2748 | 2368 | 1493 |
| p value | 0.21 | 0.27 | 0.009 |
| Yield % | 85.7 | 84.0 | 54.6 |
| In the case of ColH/ColG = 10/1 | | | |
| | 3416 | 1711 | 2015 |
| | 2282 | 2517 | 2134 |
| | 2707 | 2652 | 2796 |
| | 3338 | 2821 | 3233 |
| | 3188 | 2804 | 2269 |
| | 3488 | 4653 | |
| Average value | 3070 | 2860 | 2489 |
| p value | 0.71 | 0.95 | 0.52 |
| Yield % | 95.8 | 101.5 | 91.0 |
| In the case of ColH/ColG = 10/0 | | | |
| | 1671 | 1443 | 1364 |
| | 1807 | 2350 | 2764 |
| Average value | 1739 | 1897 | 2064 |
| p value | 0.04 | 0.11 | 0.36 |
| Yield % | 54.2 | 67.3 | 75.5 |

As shown in Table 2, even in the complete absence of Col G, separation of pancreatic islets was possible in all lineages of rats. In contrast, in the complete absence of Col H, the pancreas was not digested at all in all lineages of rats. Next, the Col H/G ratio was found to have an effect on the results of the pancreatic islet separation. In the case where the H/G ratio was set at 1/10, the yield of separated pancreatic islets significantly decreases only in the Wistar group (54.6% of the reference ratio, p=0.009). Furthermore, also in the complete absence of Col G, a sufficient yield of separated pancreatic islets was obtained in the order of Wistar (75.5%), SD (67.3%), and Lewis (54.2%). The expression of a substrate requiring Col H had a tendency of Wistar>SD>Lewis.

As described above, it was demonstrated that if the optimal use-amount ratio of ColH and ColG was calculated to optimize ColG and ColH use amounts, pancreatic islets can be separated in high yield.

Reference Example

Effect of the Collagenase Ratio (ColH/ColG) on Separation of Pancreatic Islets

Separation of pancreatic islets was performed by changing the collagenase ratio (ColH/ColG) of two collagenases used in separation of pancreatic islets of rats to be 0, 0.05, 0.1, 0.2, and 0.4. As a result, in ATP/DNA, in-vitro carbohydrate tolerance test and Insulin/DNA experiment (which show yield and quality), it was confirmed that high-quality pancreatic islets can be separated in high yield in the range of collagenase ratio from 0.1 to 0.2.

Figure 14:
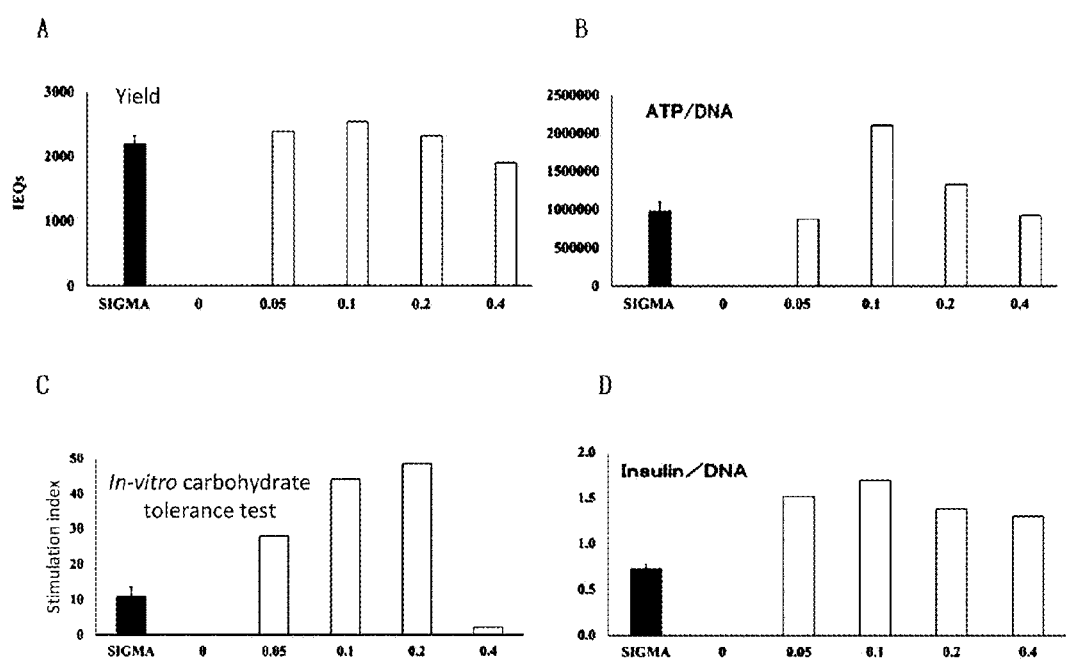
FIG. 14 shows the effect of difference in the composition ratio of collagenases G and H on the quantity and quality of pancreatic islets (A: yield, B: ATP/DNA, C: In-vitro carbohydrate tolerance test, D: Insulin/DNA).

The results are shown in FIG. 14. FIG. 14A shows yield. FIG. 14B shows ATP/DNA, which is a corrected value of energy charge (ATP) by the size (DNA) of the pancreatic islet. The In-vitro carbohydrate tolerance test of FIG. 14C shows insulin secretion ability of pancreatic islets in response to glucose, and represents an extra action of pancreatic islets. Insulin/DNA shown in FIG. 14D is a corrected value of insulin amount by the size (DNA) of the pancreatic islet. If a reagent or the like is toxic to pancreatic islets, degranulation of pancreatic islets often occurs. Therefore, this is positioned as a kind of toxicity test for pancreatic islets.

It has been reported that as the enzyme for separating pancreatic islets, two types of collagenases (ColG and ColH) produced by *Clostridium histolyticum* and a neutral metal protease are suitable (Diabetes: 46:1120:1997). The above results teach that the combination ratio of two types of collagenases (ColG and ColH) is an important factor for determining the yield and quality of pancreatic islet separation.

The optimal combination ratio of collagenases varies depending upon the animal other than a rat such as a pig and a human even if individuals belong to the same species, and is thus a factor decreasing a success rate in isolation of pancreatic islets. Therefore, if the optimal combination ratio of collagenases to be used is determined by using the probes of the present invention before pancreatic islets are separated, it is possible to calculate the use amounts of collagenases to be employed and carry out pancreatic islet separation in an optimal combination ratio, with the result that high quality pancreatic islets can be obtained in high yield.

INDUSTRIAL APPLICABILITY

According to the present invention, it is possible to accurately and easily determine the type and amount of protease to be used from the protein composition of the extracellular matrix or organ to be separated, and isolate desired cells and the like while maintaining high activity. Therefore, the present invention is useful in a wide variety of uses in the field of therapy, diagnosis and examination including organ transplantation such as pancreatic islet transplantation, regenerative medicine by cell transplantation and establishment of cell strains.

All publications, patents and patent applications cited in the specification are incorporated in their entirety as a reference.

SEQUENCE LISTING FREE TEXT

SEQ ID NO: 3: Oligo DNA
SEQ ID NO: 4: Oligo DNA
SEQ ID NO: 5: Forward primer for ColGCBD (primer 1)
SEQ ID NO: 6: Reverse primer for ColGCBD (primer 2)
SEQ ID NO: 7: Forward primer for EGFP (primer 3)
SEQ ID NO: 8: Reverse primer for EGFP (primer 4)
SEQ ID NO: 9: EGFP-ColGCBD
SEQ ID NO: 10: EGFP-ColGCBD
SEQ ID NO: 11: Oligo DNA
SEQ ID NO: 12: Oligo DNA
SEQ ID NO: 13: Forward primer for ColHCBD (primer 5)
SEQ ID NO: 14: Reverse primer for ColHCBD (primer 6)
SEQ ID NO: 15: Forward primer for DsRed (primer 7)
SEQ ID NO: 16: Reverse primer for DsRed (primer 8)
SEQ ID NO: 17: DsRed-ColHCBD
SEQ ID NO: 18: DsRed-ColHCBD
SEQ ID NO: 19: Forward primer for amplification of tdTomatogene (TomatoF)
SEQ ID NO: 20: Reverse primer for amplification of tdTomatogene (TomatoR)

REFERENCE TO A "SEQUENCE LISTING," A TABLE, OR A COMPUTER PROGRAM LISTING APPENDIX SUBMITTED AS AN ASCII TEXT FILE

The material in the ASCII text file, named "OHNO2-51212-Sequence-Project-ST25.txt", created Sep. 5, 2013, file size of 36,864 bytes, is hereby incorporated by reference.

The invention claimed is:

1. A method for separating cells or cell populations from a biological tissue, comprising:
  applying two or more probes respectively containing biological-component binding domains of two or more proteases and two or more visualization molecules to an isolated biological tissue,
  measuring binding amounts of the probes to the biological tissue through the visualization molecules,
  determining a quantitative ratio of the proteases based on results of the measurement,
  applying the proteases in the quantitative ratio to the biological tissue, and
  separating the cells or the cell populations from the biological tissue,
  wherein each of the proteases is selected from the group consisting of collagenase, trypsin, chymotrypsin, dispase, elastase, papain, pronase, thermolysin, subtilisin, bromelain, phytin, and thermitase, and
  wherein each of the two or more visualization molecules is a molecule that is different from the other two or more visualization molecules and that is selected from the group consisting of fluorescent molecules, luminescent molecules, and radioisotopes including a positron nuclide.

2. The method according to claim 1, wherein at least one of the two or more visualization molecules is a luciferase protein and/or fluorescent molecule selected from the group consisting of GFP, EGFP, YFP, BFP, CFP, DsRED, tdTomato, and RFP.

3. The method according to claim 2, wherein the luciferase protein has a peak wavelength and luminescent intensity different from a wild-type luciferase.

4. The method according to claim 2, wherein the luciferase protein is linked to a fluorescent molecule selected from the group consisting of GFP, EGFP, YFP, BFP, CFP, DsRED, tdTomato, and RFP via a linker.

5. The method according to claim 1, wherein each of the biological-component binding domains and the visualization molecules form a fusion protein.

6. The method according to claim 1, wherein each of the biological-component binding domains comprises a collagen binding domain of the proteases.

7. The method according to claim 6, wherein the collagen binding domains are collagen binding domains of collagenases selected from collagenases derived from the genus *Clostridium*.

8. The method according to claim 7, wherein the collagen binding domains are collagen binding domains of collagenase G and collagenase H derived from *Clostridium histolyticum*.

9. The method according to claim 1, comprising: applying the two or more probes separately to a biological tissue, and measuring binding amounts of the probes separately.

10. The method according to claim 1, comprising: applying the two or more probes simultaneously to a biological tissue, and measuring binding amounts of the probes simultaneously.

11. The method according to claim 1, wherein the probes each contain 1 to 20 repeats of a biological-component binding domain.

12. A method for separating cells or cell populations from a biological tissue, comprising:
applying two or more probes respectively containing collagen binding domains of two or more collagenases and two or more visualization molecules to an isolated biological tissue,
measuring binding amounts of the probes to the biological tissue through the visualization molecules,
determining a quantitative ratio of the collagenases based on results of the measurement,
applying the collagenases in the quantitative ratio to the biological tissue, and
separating the cells or the cell populations from the biological tissue,
wherein each of the two or more visualization molecules is a molecule that is different from the other two or more visualization molecules and that is selected from the group consisting of fluorescent molecules, luminescent molecules, and radioisotopes including a positron nuclide.

13. The method according to claim 12, wherein at least one of the two or more visualization molecules is a luciferase protein and/or fluorescent molecule selected from the group consisting of GFP, EGFP, YFP, BFP, CFP, DsRED, tdTomato, and RFP.

14. The method according to claim 12, wherein the collagen binding domains are collagen binding domains of collagenases selected from collagenases derived from the genus *Clostridium*.

15. The method according to claim 14, wherein the collagen binding domains are collagen binding domains of collagenase G and collagenase H derived from *Clostridium histolyticum*.

* * * * *

UNITED STATES PATENT AND TRADEMARK OFFICE
CERTIFICATE OF CORRECTION

PATENT NO. : 9,354,240 B2  
APPLICATION NO. : 14/003495  
DATED : May 31, 2016  
INVENTOR(S) : Yamagata et al.

Page 1 of 1

It is certified that error appears in the above-identified patent and that said Letters Patent is hereby corrected as shown below:

In the specification:

Column 8, line 57: please delete "$^{13}C$" and replace it with -- $^{11}C$ --

Column 14, line 49: please delete "ill" and replace it with -- μl --

Signed and Sealed this
Twenty-sixth Day of July, 2016

Michelle K. Lee
*Director of the United States Patent and Trademark Office*

SEQUENCE LISTING

```
<160> NUMBER OF SEQ ID NOS: 22

<210> SEQ ID NO 1
<211> LENGTH: 236
<212> TYPE: PRT
<213> ORGANISM: Clostridium histolyticum

<400> SEQUENCE: 1

Thr Thr Thr Pro Ile Thr Lys Glu Met Glu Pro Asn Asp Asp Ile Lys
1               5                   10                  15

Glu Ala Asn Gly Pro Ile Val Glu Gly Val Thr Val Lys Gly Asp Leu
            20                  25                  30

Asn Gly Ser Asp Asp Ala Asp Thr Phe Tyr Phe Asp Val Lys Glu Asp
        35                  40                  45
```

```
Gly Asp Val Thr Ile Glu Leu Pro Tyr Ser Gly Ser Ser Asn Phe Thr
     50                  55                  60

Trp Leu Val Tyr Lys Glu Gly Asp Gln Asn His Ile Ala Ser Gly
 65                  70                  75                  80

Ile Asp Lys Asn Asn Ser Lys Val Gly Thr Phe Lys Ser Thr Lys Gly
                 85                  90                  95

Arg His Tyr Val Phe Ile Tyr Lys His Asp Ser Ala Ser Asn Ile Ser
            100                 105                 110

Tyr Ser Leu Asn Ile Lys Gly Leu Gly Asn Glu Lys Leu Lys Glu Lys
        115                 120                 125

Glu Asn Asn Asp Ser Ser Asp Lys Ala Thr Val Ile Pro Asn Phe Asn
130                 135                 140

Thr Thr Met Gln Gly Ser Leu Leu Gly Asp Asp Ser Arg Asp Tyr Tyr
145                 150                 155                 160

Ser Phe Glu Val Lys Glu Gly Glu Val Asn Ile Glu Leu Asp Lys
                165                 170                 175

Lys Asp Glu Phe Gly Val Thr Trp Thr Leu His Pro Gly Ser Asn Ile
            180                 185                 190

Asn Asp Arg Ile Thr Tyr Gly Gln Val Asp Gly Asn Lys Val Ser Asn
        195                 200                 205

Lys Val Lys Leu Arg Pro Gly Lys Tyr Tyr Leu Leu Val Tyr Lys Tyr
210                 215                 220

Ser Gly Ser Gly Asn Tyr Glu Leu Arg Val Asn Lys
225                 230                 235

<210> SEQ ID NO 2
<211> LENGTH: 219
<212> TYPE: PRT
<213> ORGANISM: Clostridium histolyticum

<400> SEQUENCE: 2

Thr Thr Thr Ala Glu Ile Lys Asp Leu Ser Glu Asn Lys Leu Pro Val
  1               5                  10                  15

Ile Tyr Met His Val Pro Lys Ser Gly Ala Leu Asn Gln Lys Val Val
             20                  25                  30

Phe Tyr Gly Lys Gly Thr Tyr Asp Pro Asp Gly Ser Ile Ala Gly Tyr
         35                  40                  45

Gln Trp Asp Phe Gly Asp Gly Ser Asp Phe Ser Ser Glu Gln Asn Pro
     50                  55                  60

Ser His Val Tyr Thr Lys Lys Gly Glu Tyr Thr Val Thr Leu Arg Val
 65                  70                  75                  80

Met Asp Ser Ser Gly Gln Met Ser Glu Lys Thr Met Lys Ile Lys Ile
                 85                  90                  95

Thr Asp Pro Val Tyr Pro Ile Gly Thr Glu Lys Glu Pro Asn Asn Ser
            100                 105                 110

Lys Glu Thr Ala Ser Gly Pro Ile Val Pro Gly Ile Pro Val Ser Gly
        115                 120                 125

Thr Ile Glu Asn Thr Ser Asp Gln Asp Tyr Phe Tyr Phe Asp Val Ile
130                 135                 140

Thr Pro Gly Glu Val Lys Ile Asp Ile Asn Lys Leu Gly Tyr Gly Gly
145                 150                 155                 160

Ala Thr Trp Val Val Tyr Asp Glu Asn Asn Ala Val Ser Tyr Ala
                165                 170                 175

Thr Asp Asp Gly Gln Asn Leu Ser Gly Lys Phe Lys Ala Asp Lys Pro
            180                 185                 190
```

```
Gly Arg Tyr Tyr Ile His Leu Tyr Met Phe Asn Gly Ser Tyr Met Pro
    195                 200                 205

Tyr Arg Ile Asn Ile Glu Gly Ser Val Gly Arg
    210                 215
```

```
<210> SEQ ID NO 3
<211> LENGTH: 30
<212> TYPE: DNA
<213> ORGANISM: Artificial
<220> FEATURE:
<223> OTHER INFORMATION: oligo DNA

<400> SEQUENCE: 3
tcgacgatta taaagatgat gatgataaat                                   30

<210> SEQ ID NO 4
<211> LENGTH: 30
<212> TYPE: DNA
<213> ORGANISM: Artificial
<220> FEATURE:
<223> OTHER INFORMATION: oligo DNA

<400> SEQUENCE: 4
ctagatttat catcatcatc tttataatcg                                   30

<210> SEQ ID NO 5
<211> LENGTH: 35
<212> TYPE: DNA
<213> ORGANISM: Artificial
<220> FEATURE:
<223> OTHER INFORMATION: forward primer for ColGCBD (primer1)

<400> SEQUENCE: 5
aaagaacgga tccacaacaa cacctataac taaag                             35

<210> SEQ ID NO 6
<211> LENGTH: 38
<212> TYPE: DNA
<213> ORGANISM: Artificial
<220> FEATURE:
<223> OTHER INFORMATION: reverse primer for ColGCBD (primer2)

<400> SEQUENCE: 6
aagcagagat gaattcttta tttaccctta actcatag                          38

<210> SEQ ID NO 7
<211> LENGTH: 29
<212> TYPE: DNA
<213> ORGANISM: Artificial
<220> FEATURE:
<223> OTHER INFORMATION: forward primer for EGFP (primer3)

<400> SEQUENCE: 7
cgaaggtgag ctcatggtga gcaagggcg                                    29

<210> SEQ ID NO 8
<211> LENGTH: 29
<212> TYPE: DNA
<213> ORGANISM: Artificial
<220> FEATURE:
<223> OTHER INFORMATION: reverse primer for EGFP (primer4)

<400> SEQUENCE: 8
agactgcggt accgatcgat ctgagtccg                                    29
```

<210> SEQ ID NO 9
<211> LENGTH: 1554
<212> TYPE: DNA
<213> ORGANISM: Artificial
<220> FEATURE:
<223> OTHER INFORMATION: EGFP-ColGCBD
<220> FEATURE:
<221> NAME/KEY: CDS
<222> LOCATION: (1)..(1554)
<220> FEATURE:
<221> NAME/KEY: misc_feature
<222> LOCATION: (1)..(15)
<223> OTHER INFORMATION: TEE sequence
<220> FEATURE:
<221> NAME/KEY: misc_feature
<222> LOCATION: (16)..(33)
<223> OTHER INFORMATION: His-tag
<220> FEATURE:
<221> NAME/KEY: misc_feature
<222> LOCATION: (43)..(777)
<223> OTHER INFORMATION: EGFP sequence
<220> FEATURE:
<221> NAME/KEY: misc_feature
<222> LOCATION: (796)..(1503)
<223> OTHER INFORMATION: ColGCBD sequence
<220> FEATURE:
<221> NAME/KEY: misc_feature
<222> LOCATION: (1522)..(1545)
<223> OTHER INFORMATION: Flag sequence

<400> SEQUENCE: 9

| | | |
|---|---|---|
| atg aat cat aaa gtg cat cat cat cat cat cat atg gag ctc atg gtg<br>Met Asn His Lys Val His His His His His His Met Glu Leu Met Val<br>1            5                      10                 15 | | 48 |
| agc aag ggc gag gag ctg ttc acc ggg gtg gtg ccc atc ctg gtc gag<br>Ser Lys Gly Glu Glu Leu Phe Thr Gly Val Val Pro Ile Leu Val Glu<br>                20                      25                      30 | | 96 |
| ctg gac ggc gac gta aac ggc cac aag ttc agc gtg tcc ggc gag ggc<br>Leu Asp Gly Asp Val Asn Gly His Lys Phe Ser Val Ser Gly Glu Gly<br>        35                      40                      45 | | 144 |
| gag ggc gat gcc acc tac ggc aag ctg acc ctg aag ttc atc tgc acc<br>Glu Gly Asp Ala Thr Tyr Gly Lys Leu Thr Leu Lys Phe Ile Cys Thr<br> 50                      55                      60 | | 192 |
| acc ggc aag ctg ccc gtg ccc tgg ccc acc ctc gtg acc acc ctg acc<br>Thr Gly Lys Leu Pro Val Pro Trp Pro Thr Leu Val Thr Thr Leu Thr<br>65                70                      75                      80 | | 240 |
| tac ggc gtg cag tgc ttc agc cgc tac ccc gac cac atg aag cag cac<br>Tyr Gly Val Gln Cys Phe Ser Arg Tyr Pro Asp His Met Lys Gln His<br>                85                      90                      95 | | 288 |
| gac ttc ttc aag tcc gcc atg ccc gaa ggc tac gtc cag gag cgc acc<br>Asp Phe Phe Lys Ser Ala Met Pro Glu Gly Tyr Val Gln Glu Arg Thr<br>        100                      105                    110 | | 336 |
| atc ttc ttc aag gac gac ggc aac tac aag acc cgc gcc gag gtg aag<br>Ile Phe Phe Lys Asp Asp Gly Asn Tyr Lys Thr Arg Ala Glu Val Lys<br>           115                      120                    125 | | 384 |
| ttc gag ggc gac acc ctg gtg aac cgc atc gag ctg aag ggc atc gac<br>Phe Glu Gly Asp Thr Leu Val Asn Arg Ile Glu Leu Lys Gly Ile Asp<br>    130                      135                    140 | | 432 |
| ttc aag gag gac ggc aac atc ctg ggg cac aag ctg gag tac aac tac<br>Phe Lys Glu Asp Gly Asn Ile Leu Gly His Lys Leu Glu Tyr Asn Tyr<br>145              150                      155                    160 | | 480 |
| aac agc cac aac gtc tat atc atg gcc gac aag cag aag aac ggc atc<br>Asn Ser His Asn Val Tyr Ile Met Ala Asp Lys Gln Lys Asn Gly Ile<br>                165                      170                    175 | | 528 |
| aag gtg aac ttc aag atc cgc cac aac atc gag gac ggc agc gtg cag<br>Lys Val Asn Phe Lys Ile Arg His Asn Ile Glu Asp Gly Ser Val Gln | | 576 |

```
      180                 185                 190
ctc gcc gac cac tac cag cag aac acc ccc atc ggc gac ggc ccc gtg    624
Leu Ala Asp His Tyr Gln Gln Asn Thr Pro Ile Gly Asp Gly Pro Val
    195                 200                 205 ctg ctg ccc gac aac cac tac ctg agc acc cag tcc gcc ctg agc aaa    672
Leu Leu Pro Asp Asn His Tyr Leu Ser Thr Gln Ser Ala Leu Ser Lys
210                 215                 220 gac ccc aac gag aag cgc gat cac atg gtc ctg ctg gag ttc gtg acc    720
Asp Pro Asn Glu Lys Arg Asp His Met Val Leu Leu Glu Phe Val Thr
225                 230                 235                 240 gcc gcc ggg atc act ctc ggc atg gac gag ctg tac aag tcc gga ctc    768
Ala Ala Gly Ile Thr Leu Gly Met Asp Glu Leu Tyr Lys Ser Gly Leu
                245                 250                 255 aga tcg atc ggt acc ctc gag gga tcc aca aca aca cct ata act aaa    816
Arg Ser Ile Gly Thr Leu Glu Gly Ser Thr Thr Thr Pro Ile Thr Lys
                260                 265                 270 gaa atg gaa cct aat gat gat ata aaa gag gct aat ggt cca ata gtt    864
Glu Met Glu Pro Asn Asp Asp Ile Lys Glu Ala Asn Gly Pro Ile Val
                275                 280                 285 gaa ggt gtt act gta aaa ggt gat tta aat ggt tct gat gat gct gat    912
Glu Gly Val Thr Val Lys Gly Asp Leu Asn Gly Ser Asp Asp Ala Asp
    290                 295                 300 acc ttc tat ttt gat gta aaa gaa gat ggt gat gtt aca att gaa ctt    960
Thr Phe Tyr Phe Asp Val Lys Glu Asp Gly Asp Val Thr Ile Glu Leu
305                 310                 315                 320 cct tat tca ggg tca tct aat ttc aca tgg tta gtt tat aaa gag gga    1008
Pro Tyr Ser Gly Ser Ser Asn Phe Thr Trp Leu Val Tyr Lys Glu Gly
                325                 330                 335 gac gat caa aac cat att gca agt ggt ata gat aag aat aac tca aaa    1056
Asp Asp Gln Asn His Ile Ala Ser Gly Ile Asp Lys Asn Asn Ser Lys
                340                 345                 350 gtt gga aca ttt aaa tct aca aaa gga aga cat tat gtg ttt ata tat    1104
Val Gly Thr Phe Lys Ser Thr Lys Gly Arg His Tyr Val Phe Ile Tyr
                355                 360                 365 aaa cac gat tct gct tca aat ata tcc tat tct tta aac ata aaa gga    1152
Lys His Asp Ser Ala Ser Asn Ile Ser Tyr Ser Leu Asn Ile Lys Gly
    370                 375                 380 tta ggt aac gag aaa ttg aag gaa aaa gaa aat aat gat tct tct gat    1200
Leu Gly Asn Glu Lys Leu Lys Glu Lys Glu Asn Asn Asp Ser Ser Asp
385                 390                 395                 400 aaa gct aca gtt ata cca aat ttc aat acc act atg caa ggt tca ctt    1248
Lys Ala Thr Val Ile Pro Asn Phe Asn Thr Thr Met Gln Gly Ser Leu
                405                 410                 415 tta ggt gat gat tca aga gat tat tat tct ttt gag gtt aag gaa gaa    1296
Leu Gly Asp Asp Ser Arg Asp Tyr Tyr Ser Phe Glu Val Lys Glu Glu
                420                 425                 430 ggc gaa gtt aat ata gaa cta gat aaa aag gat gaa ttt ggt gta aca    1344
Gly Glu Val Asn Ile Glu Leu Asp Lys Lys Asp Glu Phe Gly Val Thr
                435                 440                 445 tgg aca cta cat cca gag tca aat att aat gac aga ata act tac gga    1392
Trp Thr Leu His Pro Glu Ser Asn Ile Asn Asp Arg Ile Thr Tyr Gly
    450                 455                 460 caa gtt gat ggt aat aag gta tct aat aaa gtt aaa tta aga cca gga    1440
Gln Val Asp Gly Asn Lys Val Ser Asn Lys Val Lys Leu Arg Pro Gly
465                 470                 475                 480 aaa tat tat cta ctt gtt tat aaa tac tca gga tca gga aac tat gag    1488
Lys Tyr Tyr Leu Leu Val Tyr Lys Tyr Ser Gly Ser Gly Asn Tyr Glu
                485                 490                 495 tta agg gta aat aaa gaa ttc aag ctt gtc gac gat tat aaa gat gat    1536
Leu Arg Val Asn Lys Glu Phe Lys Leu Val Asp Asp Tyr Lys Asp Asp
```

```
Leu Arg Val Asn Lys Glu Phe Lys Leu Val Asp Asp Tyr Lys Asp Asp
                500                 505                 510 gat gat aaa tct aga tag                                              1554
Asp Asp Lys Ser Arg
        515
```

<210> SEQ ID NO 10
<211> LENGTH: 517
<212> TYPE: PRT
<213> ORGANISM: Artificial
<220> FEATURE:
<223> OTHER INFORMATION: EGFP-ColGCBD

<400> SEQUENCE: 10

```
Met Asn His Lys Val His His His His His Met Glu Leu Met Val
1               5                   10                  15

Ser Lys Gly Glu Glu Leu Phe Thr Gly Val Val Pro Ile Leu Val Glu
                20                  25                  30

Leu Asp Gly Asp Val Asn Gly His Lys Phe Ser Val Ser Gly Glu Gly
            35                  40                  45

Glu Gly Asp Ala Thr Tyr Gly Lys Leu Thr Leu Lys Phe Ile Cys Thr
    50                  55                  60

Thr Gly Lys Leu Pro Val Pro Trp Pro Thr Leu Val Thr Thr Leu Thr
65                  70                  75                  80

Tyr Gly Val Gln Cys Phe Ser Arg Tyr Pro Asp His Met Lys Gln His
                85                  90                  95

Asp Phe Phe Lys Ser Ala Met Pro Glu Gly Tyr Val Gln Glu Arg Thr
            100                 105                 110

Ile Phe Phe Lys Asp Asp Gly Asn Tyr Lys Thr Arg Ala Glu Val Lys
        115                 120                 125

Phe Glu Gly Asp Thr Leu Val Asn Arg Ile Glu Leu Lys Gly Ile Asp
    130                 135                 140

Phe Lys Glu Asp Gly Asn Ile Leu Gly His Lys Leu Glu Tyr Asn Tyr
145                 150                 155                 160

Asn Ser His Asn Val Tyr Ile Met Ala Asp Lys Gln Lys Asn Gly Ile
                165                 170                 175

Lys Val Asn Phe Lys Ile Arg His Asn Ile Glu Asp Gly Ser Val Gln
            180                 185                 190

Leu Ala Asp His Tyr Gln Gln Asn Thr Pro Ile Gly Asp Gly Pro Val
        195                 200                 205

Leu Leu Pro Asp Asn His Tyr Leu Ser Thr Gln Ser Ala Leu Ser Lys
    210                 215                 220

Asp Pro Asn Glu Lys Arg Asp His Met Val Leu Leu Glu Phe Val Thr
225                 230                 235                 240

Ala Ala Gly Ile Thr Leu Gly Met Asp Glu Leu Tyr Lys Ser Gly Leu
                245                 250                 255

Arg Ser Ile Gly Thr Leu Glu Gly Ser Thr Thr Thr Pro Ile Thr Lys
            260                 265                 270

Glu Met Glu Pro Asn Asp Asp Ile Lys Glu Ala Asn Gly Pro Ile Val
        275                 280                 285

Glu Gly Val Thr Val Lys Gly Asp Leu Asn Gly Ser Asp Asp Ala Asp
    290                 295                 300

Thr Phe Tyr Phe Asp Val Lys Glu Asp Gly Asp Val Thr Ile Glu Leu
305                 310                 315                 320

Pro Tyr Ser Gly Ser Ser Asn Phe Thr Trp Leu Val Tyr Lys Glu Gly
                325                 330                 335
```

```
Asp Asp Gln Asn His Ile Ala Ser Gly Ile Asp Lys Asn Asn Ser Lys
             340                 345                 350

Val Gly Thr Phe Lys Ser Thr Lys Gly Arg His Tyr Val Phe Ile Tyr
         355                 360                 365

Lys His Asp Ser Ala Ser Asn Ile Ser Tyr Ser Leu Asn Ile Lys Gly
     370                 375                 380

Leu Gly Asn Glu Lys Leu Lys Glu Lys Glu Asn Asn Asp Ser Ser Asp
385                 390                 395                 400

Lys Ala Thr Val Ile Pro Asn Phe Asn Thr Thr Met Gln Gly Ser Leu
                 405                 410                 415

Leu Gly Asp Ser Arg Asp Tyr Tyr Ser Phe Glu Val Lys Glu Glu
             420                 425                 430

Gly Glu Val Asn Ile Glu Leu Asp Lys Lys Asp Glu Phe Gly Val Thr
         435                 440                 445

Trp Thr Leu His Pro Glu Ser Asn Ile Asn Asp Arg Ile Thr Tyr Gly
     450                 455                 460

Gln Val Asp Gly Asn Lys Val Ser Asn Lys Val Lys Leu Arg Pro Gly
465                 470                 475                 480

Lys Tyr Tyr Leu Leu Val Tyr Lys Tyr Ser Gly Ser Gly Asn Tyr Glu
                 485                 490                 495

Leu Arg Val Asn Lys Glu Phe Lys Leu Val Asp Asp Tyr Lys Asp Asp
             500                 505                 510

Asp Asp Lys Ser Arg
        515

<210> SEQ ID NO 11
<211> LENGTH: 36
<212> TYPE: DNA
<213> ORGANISM: Artificial
<220> FEATURE:
<223> OTHER INFORMATION: oligo DNA

<400> SEQUENCE: 11
tcgacgaaca gaaactgatt agcgaagaag atctgt                              36

<210> SEQ ID NO 12
<211> LENGTH: 36
<212> TYPE: DNA
<213> ORGANISM: Artificial
<220> FEATURE:
<223> OTHER INFORMATION: oligo DNA

<400> SEQUENCE: 12
ctagacagat cttcttcgct aatcagtttc tgttcg                              36

<210> SEQ ID NO 13
<211> LENGTH: 36
<212> TYPE: DNA
<213> ORGANISM: Artificial
<220> FEATURE:
<223> OTHER INFORMATION: forward primer for ColHCBD (primer5)

<400> SEQUENCE: 13
gaatcttcag gatccactac tactgcagaa ataaag                              36

<210> SEQ ID NO 14
<211> LENGTH: 45
<212> TYPE: DNA
<213> ORGANISM: Artificial
<220> FEATURE:
```

-continued

<223> OTHER INFORMATION: reverse primer for ColHCBD (primer6)

<400> SEQUENCE: 14
aagcagagat gaattctctt cctactgaac cttctatatt aattc                45

<210> SEQ ID NO 15
<211> LENGTH: 31
<212> TYPE: DNA
<213> ORGANISM: Artificial
<220> FEATURE:
<223> OTHER INFORMATION: forward primer for DsRED (primer7)

<400> SEQUENCE: 15
gtaccggtcg agctcatgga caacaccgag g                                31

<210> SEQ ID NO 16
<211> LENGTH: 32
<212> TYPE: DNA
<213> ORGANISM: Artificial
<220> FEATURE:
<223> OTHER INFORMATION: forward primer for DsRED (primer8)

<400> SEQUENCE: 16
gtcgcggccg gtaccctggg agccggagtg gc                               32

<210> SEQ ID NO 17
<211> LENGTH: 1449
<212> TYPE: DNA
<213> ORGANISM: Artificial
<220> FEATURE:
<223> OTHER INFORMATION: DsRed-CoHCBD
<220> FEATURE:
<221> NAME/KEY: CDS
<222> LOCATION: (1)..(1449)
<220> FEATURE:
<221> NAME/KEY: misc_feature
<222> LOCATION: (1)..(15)
<223> OTHER INFORMATION: TEE sequence
<220> FEATURE:
<221> NAME/KEY: misc_feature
<222> LOCATION: (16)..(33)
<223> OTHER INFORMATION: His-tag
<220> FEATURE:
<221> NAME/KEY: misc_feature
<222> LOCATION: (43)..(717)
<223> OTHER INFORMATION: DsRed sequence
<220> FEATURE:
<221> NAME/KEY: misc_feature
<222> LOCATION: (736)..(1392)
<223> OTHER INFORMATION: ColHCBD sequence
<220> FEATURE:
<221> NAME/KEY: misc_feature
<222> LOCATION: (1411)..(1440)
<223> OTHER INFORMATION: C-myc sequence

<400> SEQUENCE: 17

| atg | aat | cat | aaa | gtg | cat | cat | cat | cat | cat | cat | atg | gag | ctc | atg | gac | 48 |
|---|---|---|---|---|---|---|---|---|---|---|---|---|---|---|---|---|
| Met | Asn | His | Lys | Val | His | His | His | His | His | His | Met | Glu | Leu | Met | Asp | |
| 1 | | | | 5 | | | | | 10 | | | | | 15 | | |

| aac | acc | gag | gac | gtc | atc | aag | gag | ttc | atg | cag | ttc | aag | gtg | cgc | atg | 96 |
|---|---|---|---|---|---|---|---|---|---|---|---|---|---|---|---|---|
| Asn | Thr | Glu | Asp | Val | Ile | Lys | Glu | Phe | Met | Gln | Phe | Lys | Val | Arg | Met | |
| | | | 20 | | | | | 25 | | | | | 30 | | | |

| gag | ggc | tcc | gtg | aac | ggc | cac | tac | ttc | gag | atc | gag | ggc | gag | ggc | gag | 144 |
|---|---|---|---|---|---|---|---|---|---|---|---|---|---|---|---|---|
| Glu | Gly | Ser | Val | Asn | Gly | His | Tyr | Phe | Glu | Ile | Glu | Gly | Glu | Gly | Glu | |
| | | 35 | | | | | 40 | | | | | 45 | | | | |

| ggc | aag | ccc | tac | gag | ggc | acc | cag | acc | gcc | aag | ctg | cag | gtg | acc | aag | 192 |
|---|---|---|---|---|---|---|---|---|---|---|---|---|---|---|---|---|
| Gly | Lys | Pro | Tyr | Glu | Gly | Thr | Gln | Thr | Ala | Lys | Leu | Gln | Val | Thr | Lys | |
| 50 | | | | | 55 | | | | | 60 | | | | | | |

-continued

| | | |
|---|---|---|
| ggc ggc ccc ctg ccc ttc gcc tgg gac atc ctg tcc ccc cag ttc cag<br>Gly Gly Pro Leu Pro Phe Ala Trp Asp Ile Leu Ser Pro Gln Phe Gln<br>65                         70                    75                    80 | 240 |
| gcc ggc tcc aag gcc tac gtg aag cac ccc gcc gac atc ccc gac tac<br>Ala Gly Ser Lys Ala Tyr Val Lys His Pro Ala Asp Ile Pro Asp Tyr<br>                    85                    90                    95 | 288 |
| atg aag ctg tcc ttc ccc gag ggc ttc acc tgg gag cgc tcc atg aac<br>Met Lys Leu Ser Phe Pro Glu Gly Phe Thr Trp Glu Arg Ser Met Asn<br>                    100                 105                 110 | 336 |
| ttc gag gac ggc ggc gtg gtg gag gtg cag cag gac tcc tcc ctg cag<br>Phe Glu Asp Gly Gly Val Val Glu Val Gln Gln Asp Ser Ser Leu Gln<br>           115                      120                 125 | 384 |
| gac ggc acc ttc atc tac aag gtg aag ttc aag ggc gtg aac ttc ccc<br>Asp Gly Thr Phe Ile Tyr Lys Val Lys Phe Lys Gly Val Asn Phe Pro<br>130                        135                 140 | 432 |
| gcc gac ggc ccc gta atg cag aag aag act gcc ggc tgg gag ccc tcc<br>Ala Asp Gly Pro Val Met Gln Lys Lys Thr Ala Gly Trp Glu Pro Ser<br>145                       150                 155                 160 | 480 |
| acc gag aag ctg tac ccc cag gac ggc gtg ctg aag ggc gag atc tcc<br>Thr Glu Lys Leu Tyr Pro Gln Asp Gly Val Leu Lys Gly Glu Ile Ser<br>                    165                 170                 175 | 528 |
| cac gcc ctg aag ctg aag gac ggc ggc cac tac acc tgc gac ttc aag<br>His Ala Leu Lys Leu Lys Asp Gly Gly His Tyr Thr Cys Asp Phe Lys<br>           180                      185                 190 | 576 |
| acc gtg tac aag gcc aag aag ccc gtg cag ctg ccc ggc aac cac tac<br>Thr Val Tyr Lys Ala Lys Lys Pro Val Gln Leu Pro Gly Asn His Tyr<br>195                       200                 205 | 624 |
| gtg gac tcc aag ctg gac atc acc aac cac aac gag gac tac acc gtg<br>Val Asp Ser Lys Leu Asp Ile Thr Asn His Asn Glu Asp Tyr Thr Val<br>210                        215                 220 | 672 |
| gtg gag cag tac gag cac gcc gag gcc cgc cac tcc ggc tcc cag ggt<br>Val Glu Gln Tyr Glu His Ala Glu Ala Arg His Ser Gly Ser Gln Gly<br>225                       230                 235                 240 | 720 |
| acc ctc gag gga tcc act act act gca gaa ata aag gat ctt tca gaa<br>Thr Leu Glu Gly Ser Thr Thr Thr Ala Glu Ile Lys Asp Leu Ser Glu<br>                    245                 250                 255 | 768 |
| aat aaa ctt cca gtt ata tat atg cat gta cct aaa tcc gga gcc tta<br>Asn Lys Leu Pro Val Ile Tyr Met His Val Pro Lys Ser Gly Ala Leu<br>           260                      265                 270 | 816 |
| aat caa aaa gtt gtt ttc tat gga aaa gga aca tat gac cca gat gga<br>Asn Gln Lys Val Val Phe Tyr Gly Lys Gly Thr Tyr Asp Pro Asp Gly<br>275                       280                 285 | 864 |
| tct atc gca gga tat caa tgg gac ttt ggt gat gga agt gat ttt agc<br>Ser Ile Ala Gly Tyr Gln Trp Asp Phe Gly Asp Gly Ser Asp Phe Ser<br>           290                      295                 300 | 912 |
| agt gaa caa aac cca agc cat gta tat act aaa aaa ggt gaa tat act<br>Ser Glu Gln Asn Pro Ser His Val Tyr Thr Lys Lys Gly Glu Tyr Thr<br>305                       310                 315                 320 | 960 |
| gta aca tta aga gta atg gat agt agt gga caa atg agt gaa aaa act<br>Val Thr Leu Arg Val Met Asp Ser Ser Gly Gln Met Ser Glu Lys Thr<br>                    325                 330                 335 | 1008 |
| atg aag att aag att aca gat ccg gta tat cca ata ggc act gaa aaa<br>Met Lys Ile Lys Ile Thr Asp Pro Val Tyr Pro Ile Gly Thr Glu Lys<br>           340                      345                 350 | 1056 |
| gaa cca aat aac agt aaa gaa act gca agt ggt cca ata gta cca ggt<br>Glu Pro Asn Asn Ser Lys Glu Thr Ala Ser Gly Pro Ile Val Pro Gly<br>355                       360                 365 | 1104 |
| ata cct gtt agt gga acc ata gaa aat aca agt gat caa gat tat ttc<br>Ile Pro Val Ser Gly Thr Ile Glu Asn Thr Ser Asp Gln Asp Tyr Phe<br>370                       375                 380 | 1152 |

```
tat ttt gat gtt ata aca cca gga gaa gta aaa ata gat ata aat aaa      1200
Tyr Phe Asp Val Ile Thr Pro Gly Glu Val Lys Ile Asp Ile Asn Lys
385                 390                 395                 400 tta ggg tac gga gga gct act tgg gta gta tat gat gaa aat aat aat      1248
Leu Gly Tyr Gly Gly Ala Thr Trp Val Val Tyr Asp Glu Asn Asn Asn
                405                 410                 415 gca gta tct tat gcc act gat gat ggg caa aat tta agt gga aag ttt      1296
Ala Val Ser Tyr Ala Thr Asp Asp Gly Gln Asn Leu Ser Gly Lys Phe
            420                 425                 430 aag gca gat aaa cca ggt aga tat tac atc cat ctt tac atg ttt aat      1344
Lys Ala Asp Lys Pro Gly Arg Tyr Tyr Ile His Leu Tyr Met Phe Asn
        435                 440                 445 ggt agt tat atg cca tat aga att aat ata gaa ggt tca gta gga aga      1392
Gly Ser Tyr Met Pro Tyr Arg Ile Asn Ile Glu Gly Ser Val Gly Arg
    450                 455                 460 gaa ttc aag ctt gtc gac gaa cag aaa ctg att agc gaa gaa gat ctg      1440
Glu Phe Lys Leu Val Asp Glu Gln Lys Leu Ile Ser Glu Glu Asp Leu
465                 470                 475                 480 tct aga tag                                                           1449
Ser Arg <210> SEQ ID NO 18
<211> LENGTH: 482
<212> TYPE: PRT
<213> ORGANISM: Artificial
<220> FEATURE:
<223> OTHER INFORMATION: DsRed-CoHCBD

<400> SEQUENCE: 18

Met Asn His Lys Val His His His His His Met Glu Leu Met Asp
1               5                   10                  15

Asn Thr Glu Asp Val Ile Lys Glu Phe Met Gln Phe Lys Val Arg Met
                20                  25                  30

Glu Gly Ser Val Asn Gly His Tyr Phe Glu Ile Glu Gly Glu Gly Glu
            35                  40                  45

Gly Lys Pro Tyr Glu Gly Thr Gln Thr Ala Lys Leu Gln Val Thr Lys
        50                  55                  60

Gly Gly Pro Leu Pro Phe Ala Trp Asp Ile Leu Ser Pro Gln Phe Gln
65                  70                  75                  80

Ala Gly Ser Lys Ala Tyr Val Lys His Pro Ala Asp Ile Pro Asp Tyr
                85                  90                  95

Met Lys Leu Ser Phe Pro Glu Gly Phe Thr Trp Glu Arg Ser Met Asn
            100                 105                 110

Phe Glu Asp Gly Gly Val Val Glu Val Gln Gln Asp Ser Ser Leu Gln
        115                 120                 125

Asp Gly Thr Phe Ile Tyr Lys Val Lys Phe Lys Gly Val Asn Phe Pro
    130                 135                 140

Ala Asp Gly Pro Val Met Gln Lys Lys Thr Ala Gly Trp Glu Pro Ser
145                 150                 155                 160

Thr Glu Lys Leu Tyr Pro Gln Asp Gly Val Leu Lys Gly Glu Ile Ser
                165                 170                 175

His Ala Leu Lys Leu Lys Asp Gly Gly His Tyr Thr Cys Asp Phe Lys
            180                 185                 190

Thr Val Tyr Lys Ala Lys Lys Pro Val Gln Leu Pro Gly Asn His Tyr
        195                 200                 205

Val Asp Ser Lys Leu Asp Ile Thr Asn His Asn Glu Asp Tyr Thr Val
    210                 215                 220
```

Val Glu Gln Tyr Glu His Ala Glu Ala Arg His Ser Gly Ser Gln Gly
225                 230                 235                 240

Thr Leu Glu Gly Ser Thr Thr Thr Ala Glu Ile Lys Asp Leu Ser Glu
            245                 250                 255

Asn Lys Leu Pro Val Ile Tyr Met His Val Pro Lys Ser Gly Ala Leu
        260                 265                 270

Asn Gln Lys Val Val Phe Tyr Gly Lys Gly Thr Tyr Asp Pro Asp Gly
    275                 280                 285

Ser Ile Ala Gly Tyr Gln Trp Asp Phe Gly Asp Gly Ser Asp Phe Ser
290                 295                 300

Ser Glu Gln Asn Pro Ser His Val Tyr Thr Lys Lys Gly Glu Tyr Thr
305                 310                 315                 320

Val Thr Leu Arg Val Met Asp Ser Ser Gly Gln Met Ser Glu Lys Thr
            325                 330                 335

Met Lys Ile Lys Ile Thr Asp Pro Val Tyr Pro Ile Gly Thr Glu Lys
        340                 345                 350

Glu Pro Asn Asn Ser Lys Glu Thr Ala Ser Gly Pro Ile Val Pro Gly
    355                 360                 365

Ile Pro Val Ser Gly Thr Ile Glu Asn Thr Ser Asp Gln Asp Tyr Phe
370                 375                 380

Tyr Phe Asp Val Ile Thr Pro Gly Glu Val Lys Ile Asp Ile Asn Lys
385                 390                 395                 400

Leu Gly Tyr Gly Gly Ala Thr Trp Val Val Tyr Asp Glu Asn Asn Asn
            405                 410                 415

Ala Val Ser Tyr Ala Thr Asp Asp Gly Gln Asn Leu Ser Gly Lys Phe
        420                 425                 430

Lys Ala Asp Lys Pro Gly Arg Tyr Tyr Ile His Leu Tyr Met Phe Asn
    435                 440                 445

Gly Ser Tyr Met Pro Tyr Arg Ile Asn Ile Glu Gly Ser Val Gly Arg
450                 455                 460

Glu Phe Lys Leu Val Asp Glu Gln Lys Leu Ile Ser Glu Glu Asp Leu
465                 470                 475                 480

Ser Arg

<210> SEQ ID NO 19
<211> LENGTH: 34
<212> TYPE: DNA
<213> ORGANISM: Artificial
<220> FEATURE:
<223> OTHER INFORMATION: forward primer for amplifying tdTomato gene
      (TomatoF)

<400> SEQUENCE: 19
ccggtcgccc atatggtgag caagggcgag gagg                                34

<210> SEQ ID NO 20
<211> LENGTH: 34
<212> TYPE: DNA
<213> ORGANISM: Artificial
<220> FEATURE:
<223> OTHER INFORMATION: reverse primer for amplifying tdTomato gene
      (TomatoR)

<400> SEQUENCE: 20
agagtcgcgg cggatccctt gtacagctcg tcca                                34

<210> SEQ ID NO 21

```
<211> LENGTH: 755
<212> TYPE: DNA
<213> ORGANISM: Clostridium histolyticum

<400> SEQUENCE: 21
gtgcaacagc tacagaaagc tttactatag aaataaagaa cgaagataca acaacaccta      60
taactaaaga aatggaacct aatgatgata taaaagaggc taatggtcca atagttgaag     120
gtgttactgt aaaaggtgat ttaaatggtt ctgatgatgc tgataccttc tattttgatg     180
taaaagaaga tggtgatgtt acaattgaac ttccttattc agggtcatct aatttcacat     240
ggttagttta taaagaggga gacgatcaaa accatattgc aagtggtata gataagaata     300
actcaaaagt tggaacattt aaatctacaa aaggaagaca ttatgtgttt atatataaac     360
acgattctgc ttcaaatata tcctattctt taaacataaa aggattaggt aacgagaaat     420
tgaaggaaaa agaaaataat gattcttctg ataaagctac agttatacca aatttcaata     480
ccactatgca aggttcactt ttaggtgatg attcaagaga ttattattct tttgaggtta     540
aggaagaagg cgaagttaat atagaactag ataaaaagga tgaatttggt gtaacatgga     600
cactacatcc agagtcaaat attaatgaca gaataactta cggacaagtt gatggtaata     660
aggtatctaa taaagttaaa ttaagaccag gaaaatatta tctacttgtt tataaatact     720
caggatcagg aaactatgag ttaagggtaa ataaa                                755

<210> SEQ ID NO 22
<211> LENGTH: 657
<212> TYPE: DNA
<213> ORGANISM: Clostridium histolyticum

<400> SEQUENCE: 22
actactactg cagaaataaa ggatctttca gaaaataaac ttccagttat atatatgcat      60
gtacctaaat ccggagcctt aaatcaaaaa gttgttttct atggaaaagg aacatatgac     120
ccagatggat ctatcgcagg atatcaatgg gactttggtg atggaagtga ttttagcagt     180
gaacaaaacc caagccatgt atatactaaa aaaggtgaat atactgtaac attaagagta     240
atggatagta gtggacaaat gagtgaaaaa actatgaaga ttaagattac agatccggta     300
tatccaatag gcactgaaaa agaaccaaat aacagtaaag aaactgcaag tggtccaata     360
gtaccaggta tacctgttag tggaaccata gaaaatacaa gtgatcaaga ttatttctat     420
tttgatgtta taacaccagg agaagtaaaa atagatataa ataaattagg gtacggagga     480
gctacttggg tagtatatga tgaaaataat aatgcagtat cttatgccac tgatgatggg     540
caaaatttaa gtggaaagtt taaggcagat aaaccaggta gatattacat ccatctttac     600
atgtttaatg gtagttatat gccatataga attaatatag aaggttcagt aggaaga       657
```